US006200778B1

(12) United States Patent
Treco et al.

(10) Patent No.: US 6,200,778 B1
(45) Date of Patent: Mar. 13, 2001

(54) GENOMIC SEQUENCES FOR PROTEIN PRODUCTION AND DELIVERY

(75) Inventors: Douglas A. Treco, Arlington; Michael W. Heartlein, Boxborough; Richard F Selden, Wellesley, all of MA (US)

(73) Assignee: Transkaryotic Therapies, Inc., Cambridge, MA (US)

( * ) Notice: Subject to any disclaimer, the term of this patent is extended or adjusted under 35 U.S.C. 154(b) by 0 days.

(21) Appl. No.: 09/305,639

(22) Filed: May 5, 1999

Related U.S. Application Data

(60) Provisional application No. 60/084,663, filed on May 7, 1998.

(51) Int. Cl.[7] .............................. C12N 15/63; C12N 5/00; C12N 15/00; C12P 21/06; C07H 21/04
(52) U.S. Cl. ........................ 435/69.1; 435/325; 435/455; 435/320.1; 536/23.51; 536/24.1
(58) Field of Search ................................ 536/23.1, 23.51; 435/69.1, 6, 375, 455, 463, 325

(56) References Cited

U.S. PATENT DOCUMENTS

| | | | |
|---|---|---|---|
| 5,272,071 | 12/1993 | Chappel | 435/440 |
| 5,639,640 | 6/1997 | Reddy et al. | 435/325 |
| 5,641,670 | 6/1997 | Treco et al. | 435/325 |
| 5,733,761 | 3/1998 | Treco et al. | 435/440 |

OTHER PUBLICATIONS

Hillier et al., EST Accession No. W01078, Apr. 1996.*
Tanner, M. J., GenBank Accession No. X77737, Feb. 1995.*
Adams, M. D., GenBank Accession No. Ac002303, Apr. 1996.*
Esch, F.S. et al., "Cloning and DNA sequence analysis of the cDNA for the . . . ," Proc. Natl. Acad. Sci. USA, vol. 83, pp. 6681–6621, Sep. 1986.
Fiddes, John C. et al., "Isolation, cloning and sequence analysis of the cDNA . . . ," Nature, vol. 281, pp. 351–356, Oct. 4, 1979.
Fiddes, John C. et al., "The Gene Encoding the Common Alpha Subunit of the Four . . . ," Journal of Molecular and Applied Genetics; vol. 1, No. 1, p. 3–18, 1981.
Galway, Brenda A. et al., "In Vitro and in Vovo Bioactivity of Recombinant Human Follicle–Stimulating . . . ," Endocrinology, vol. 127, No. 1, p. 93–100, 1990.
GenBank Accession No. 9183319, dated Apr. 9, 1996.
Jameson, Larry J. et al., "Human Follicle–Stimulating Hormone β–Subunit Gene Encodes Multiple . . . , " Molecular Endocrinology, vol. 2, No. 9, p. 806–815, 1988.
Keene, Jeffrey L. et al., "Expression of Biologically Active Human Follitropin . . . ," The Journal of Biological Chemistry, vol. 264, No. 9, p. 4769–4775, Mar. 25, 1989.
Kourides, Ione A. et al., "The Regulation and Organization of Thyroid Stimulating . . . ," Recent Progress in Hormone Research, vol. 40, p. 79–120, 1984.
Kumar, Rajendra T. et al., "Follicle stimulating hormone is required for ovarian follicle . . . ," Nature Genetics, vol. 15, p. 201–204, Feb. 15, 1997.
Mannearts, B. et al., "Comparative in Vitro and in Vivo Studies on the Biological . . . ," Endocrinology, vol. 129, No. 5, p. 2623–2630, 1991.
Olijve, Wiebe et al., "Molecular biology and biochemistry of human recombinant follicle . . . ," Molecular Human Reproduction, vol. 2, No. 5, p. 371–382, 1996.
Stanton, P.G. et al., "Structural and functional characterisation of hFSH and hLH . . . ," Molecular and Cellular Endcrinology, vol. 125, p. 133–141, (1996).
Watkins, Paul C., "DNA Sequence and Regional Assignment of the Human Follicle–Stimulating . . . ," DNA, vol. 6, No. 3, p. 205–212, 1987.
Anon, "TKT's Plans for Turning on Endogenous Genes," Exp. Opin. Ther. Patents 8:325–328 (1998).
Hirai et al., "The Gene for the β Subunit of Porcine FSH: Absence of Consensus Oestrogen–Responsive Element and Presence of Retroposons," Journal of Molecular Endocrinology 5:147–158 (1990).

\* cited by examiner

*Primary Examiner*—Deborah J. Clark
*Assistant Examiner*—S. Chen
(74) *Attorney, Agent, or Firm*—Clark & Elbing LLP

(57) ABSTRACT

An isolated nucleic acid molecule that hybridizes under stringent conditions, or shares at least 80% sequence identity, with a defined genomic region upstream of the coding region of a FSHβ gene, and a DNA construct containing that nucleic acid molecule as a targeting sequence for homologous recombination.

37 Claims, 16 Drawing Sheets

FIG. 3A

```
       BamHI (-7453)
-7454  GGATCCGAGA ACATAGAAGG AGCAGTAAT TTATCAAGGC ATGAACACGG GTGCTTAATT TCCTATTTG
-7384  AGGCCAGGCA TGGTGGCTCA CACCTGTAAT CCCAACACTT TAGGAAGCCA AGTGGGTGG ATTGCTTGAG
-7314  TCTAGAGATTT TGAGACCAGC CTGGCCAACA TGGCGAAATC CTGTCTCTAC TAAAAATACT AAAATTAACC
-7244  AGTCATGGTG GTGGTGTGCC TTTAGTCCCA GCTACTCTGG TGGCTGAGGC ACAAGAATCA CTTGAACCTG
-7174  GGAGGCAGAG GTTGCAGTGA GCTGAGACTG TGCCACTTCA CTCCAGCCTG GGTGACAGAG TAAGATTCTG
-7104  TCTCAAAAAA TATGTATATA TACACACATA TAATAGATAC ATAAACATAT ATACATATAT AATATATAAA
-7034  TATATATATT ATATATAATA TATAAACATA TATAAAATATA TATATATATA TATATATATA TATATAAACC
-6964  AAACATAAAG GAATAATTTT GGGGAAAAT CTTCATAAAT GAAAGAACAA CATAGGCTGT TGAGTATATG
       BglII (-6879)
-6894  CACAGAAATT CAAGAGATCT TCCAGCAATT GTTTACCAGA ATTCACAAAA GAAGTCAGCT
-6824  GTGCATTTAA AGTAGAATGT GATGAGTGTT ACCACTGAGG TAGGAACTGG GAACTAAGGA AGCGTAAGAC
-6754  AGAAAGTGCT GAACTGAGAG TTGGGCATTG GAGGCTGTGT AAGGCAGAGT AAGTGAATGT CTCCTAGAAG
-6684  CTACCTTTAA ATGGAGTTTT GAAGTACTTG TTAGGTGAAA TTAGGTGAAA AGAAGAGGAG AAACATGTAT
-6614  CAGGCAGAGG GACTAGAACC TTATTACCTT CAAAGAAGAA GCAAAAAGAA TACATGTGAC TTTGAGGTGG
-6544  TGGGAGGTGC TTTAAGCCAA TATAGGTGAA TTTGACATAG GACTTCCCTA AATAATGTTC GGTCATTTGT
-6474  TAAATATATTGA GTGATATATC ACTGTATTAA AGCCCAAGAG TTGCTTTTAT ATAGAAAGAA GAAAAAAGCC
                  XbaI (-6388)           XbaI (-6372)
-6404  CAAGAGAGTT TTATTTCTAG AGGGAATATT TTCTAGAAAT AAAGGAAGGT GTATCAGCCA GTTTCTAGTC
-6334  AGGAAAAACAG AAATCACACC TGATATGCAA AATAGAGGAA AATCAGGGAA TTCATTAATC CAGAGATTG
-6264  GTTGCTCAAG TATTAGATTG CTGAAAAGCC AGACAGGGAA TATGAGGCAA TCAGAGATAA GTATTAGTGA
-6194  CAAGCTCCAT TTATGTGCAG GATTGGAGGG ACATAGGTGG GGTTCCCAGA AGCCAGAAGG TGAGACCACC
-6124  TAGCAGAAGC TCAAACCACA GCTGGGGTTT CCTCACAAAA GCTGGGACCA CCAGGAGGAG CTGTCCAATG
-6054  GGATCTGGAG CCAGGAGAT CATGCAGTCA CTACCAGGAA CTACCAGGAA ATGTAAAAGG TAGAGAGAAA
-5984  TACTCCAACT GCTTCCTTGC ATTCACTTTC CAATCTCCAT TCACAAGGC AAAAACCTGC TAATACAGCA
-5914  GAGTGGGAAA AGCAGCCTGC CAAGTCCTT TCTCCCACAA ACCAGCAC AAAACCAAGC AAAAACAAGG
-5844  AATGCATTTG ATAGCAAACA GGCTATGGAC CAACCCAACA TAAAGAAAT GATGAGTGAT TTCTTTTTC
-5774  ATTTGGTTCA AGAAAAGTAT TTCAGTAACT ATTATGTAAC AGAAATTCTA TTTATTTGG GGAATTCAAA
-5704  GGTGAATAAA AAAGAACTCT AAATTTTTAT CAATAAAATA TTTCAAAAAC CTCAATGAGA GTAATGGCAT
-5634  TAACTAGCAA ATATGCTAAT GAGATGAGCT AGCCATAAGA GGCTTAGAAT TGAGAGAAAG GTCTGGGGGC
```

```
                       PstI  (-5515)
-5564  CTCTTGACAG  GCCAAATTCA  GAGCTGTTTG  TGGGAATCTC  TGACCTAACT  GCAGGTGAA   ATATAAATAT
-5494  GGGCATTTAG  AATAGTGCC   CAAACTTTGG  ATGATTTCTG  TCTTGGGGTC  TCTCCAATTA  ATGGGATTGA
-5424  TGAGAACTGT  AGACCACTGA  GGTCACCATG  GCTCAATGAA  TAGTCCCCTG  GCTTTGAGT   CAAACTGACC
-5354  TGAATATGAA  CCCCAGCTTT  GCTACTTACA  GGTTGCATTT  ATCCTCAGTT  TTCTCATCTT  TCAAAGAAGA
-5284  ACAGTAACTT  CTTTAAAAGG  TTATGTAGG   CTGGGTGCAG  TGGCTCACGC  CTGTAATCGC  AGCACTTTGG
-5214  GAGGCGGAGG  CTAGTGGATC  ACTTGAGCC   AGGAGTTGGA  AACTAGCCTG  GCCAACATGG  TGAAACTCTG
-5144  TCTCTACAAA  AAGAAATTTA  AAAAATTTG   CTGGGTGTGG  TGGCACACAC  CTGGAATTCC  AGCTACCTGG
-5074  GAGGCCGAGG  CATGAGCATC  ACTTGAGTCT  GGAAAGCAGA  GGTTGCAGT   GAGCCAAGAT  TGTACCACTG
-5004  TACTCAAGCC  TGGGTGACAC  AGTGAGACCT  TGTCTAAAAA  AAAAAAAGGT  TATTGTGTTA  TTGTAAATAT
-4934  TGTATATGAA  CTTCTATTTA  ACATGTTTAG  TTAAATGCCT  GTGTAATTGT  CCAATGTGCT  CTTCTAGCTC
-4864  ACTGCACAGA  CAAAACTGAT  TCACTGAAT   CATGGAATTG  CAGCAAAGAA  CAAATCTAAT  TAATGTAGGT
-4794  CAAACGGGAG  GACTGAGTT   ATTATTCAAA  TCAGTCTCCC  TGAAAACTCA  GAGGCTAGGG  TTTTATGAT
-4724  AATTTGGTGG  GCAGGGACT   AGGGAATGGG  TGCTGTGAT   TGGTTGGGA   ATGAAATAGT  AAGATTGTGG
-4654  AAAACTGTCC  TCCTTCATTG  AGTCTGCTTC  CGGGTGTAGG  CCACACGACC  AGTTGAGTCA  TGAAGCATGC
-4584  GTCCAAGTGG  AGTCAGTTTG  TTGCCAGAAT  GCAAAAGCCT  GAAAAATGTC  TCAAATGATC  AACTGTAGGC
-4514  TCCACAATAA  TGATATTATC  TATAGGAGCA  ATTGGGAAG   TGTGACCTCT  GGACACATAA  CCCATAATCC
-4444  CTCCTGAACT  AGTAAGGGAT  TATAAAAACC  CTTATCAGAA  TTCAGGTCCC  GTTAGTTTTA
-4374  TAATCTCACA  GCATTTCATT  TGTTTAGAAA  GGCCATTTTC  AGTCCCTGAG  CAAGGAGGG   GTTAGTTTTA
-4304  GGATAGGACT  ATTATCCTTG  CTTCGTTAAA  CTATAAACTA  AATTCCTCCC  ATGGTTAGCT  TGGCCTACAC
-4234  CTAAGAATGA  GTGAGAACAG  CCAGCCCTGT  AGGCCTAGAGG  CAAGATGGAG  TCAGCCATGC  TAGATTTATC
-4164  TCACTGTCAT  AACCTTTGCA  AAGGCAGTTT  CACCTGGGAC  ATAGGAGGTA  CTCAATGAAA  AAGAAGCTAT
-4094  TAATATTAAA  ATTTTAAAAA  TGAATTTAAG  GAACTAGCTA  TATGTACATA  TTAGTCATTA  AAACAAAGTG
-4024  GTTCATTTAC  ATTCACACAA  ATAAATCTTG  TGATTATACA  TAGTAATAT   GAAAACTTT   GTTTCTTTC
-3954  ATAATACAAG  GTATTAGCAA  TAGATATAGT  TTTTATTA    AATGTTAGCA  TTCCTTTGA   AAAAATGAAA  AGATTATAA
-3884  TTTTCCAAGA  ATCATTAGTA  TTTTATTTA   ATATACATAA  TATAAATTT   ATTCATTCTA  TAACTTGAA
-3814  ATATGCTTGC  TTACCAATTA  CTGACAGATT  TCTATACTCA  TCAAATTCAT  CAATATTCAT  TTACATCAT
-3744  ATTGATTTGG  TACTTACAAT  GTGTACTGCT  ATGCTAAGTT  TTGTCTTTGT  CAAACATATT  TTATAAAATC
```

FIG. 3B

```
-3674 ATAATCCTAG ATGAATCCAA CTTTTGGTAA CCCACGTGCC TGAACCCTG CTGTTAACAG GCAAAGTGTG
              BglII (-3595)
-3604 GTAGGTACAG ATCTATACCT ACCACCTTCC TCTACCCACC AGCATCTGCA CCCACCACCC CTCCCCACCC
-3534 ACCATTATCT ATACCAACCA CCCCTCCCAA CCTACCAGCA TCTGCACCCA TCTGCACCCA CCACACCGCC CACACCACCAC
-3464 CATGTACACT CACTACACCT TCCAGCCATC ACCATCTGCA CCCATCACTC CTCCCCATCC ACAAGCATCT
-3394 GCACCACCA CATTTCCCTA CCTACCAGCA TCTTCACTCA CCACCTCTCC ACCCACCAGC ATCTGCACCC
-3324 ACAACCCTC CTCACCCACC AGAGTCTGCA TCCATCACAC TTGCCCACTC GCTAGCATCT GCACCATCAA
-3254 GCTCTGCCTT CTTGCCTAAT ACGGGATGAG CTCTCCATGG TTCTGCCTAA TTCTGCCACT AGACAATGCT TCCACTCCTC
-3184 TTCTATAACC CATTTCCTTT TACCTCTTCA AGTACACTTC AGAACTCTC AGAACTCTC TCTCCTTCTG ATACCAACTT
-3114 TTTCCACTTT ACTCAATCAT TCCTATCACC ATACAAACGT GTTTATTTCT CCCATCTTAA AGTTAAAAAT
-3044 CAAAGAAAA TTGTCTGCGG CCAGGCACGG TGGCTCACGC CTGTAATCCC AACACTTTGG GAGGCCAAGG
-2974 AGGGTTGAT GACTTAAGGT TAGGAGTTCA AGACCAGCCT GGCCAACATG GTGAAACCCA TCTCTACTAA
-2904 AAATACAAAA ATTAGCCAGG CATGGTGGCA GTCTCAGTTA CAGTGTCCAGGC TGAGGCCAGA
-2834 GAATGGCTTG AACCCGGGAG GCAGAGGTTG CAGTGAGCCG AGATTGTGCC CTTGCACTCC AGCCTGGGTG
-2764 ACAGAGTGAG ACTCCATCTC AAAAAAAATA AATAAAAATA AACAAAAGA AAGTTATTTT TACCAACAT
-2694 CCACATTAAC CAAATACCCA TTTCTTTATT GATCTTTGTA AAAAAAAGCT CTTTGAAAAA TTGTCTATAT
-2624 TCACTATGAC TTATCTCCTC CAAATCACTT AAACACATAC CAATCAGGTT TTTGTTTTCA TCATTCCAAA
-2554 GTAACTTTTA CAGCCAAGGA CAGTAGCGAA CTTTACATGT CATATGCATT GTGAAGTTCT TGATCCTCAT
-2484 CTTACTTAAC CTGTCAGCAG TATCTCAGAC AGTTGACAC AGGTGTCACT GGCTCCTCCC TGAGATGCTC TCTTTATTTG
-2414 GCTTTGGGGA CACCATATTC TCCCATTCC TACTTTCCTC AATGGCCCTC CTCAGTCTCC TTTGAAAGA
-2344 GGAAAAAGAA ACTTCATTAT CTCCTGGATG TAGTACAAAC AACTCAAGCT CAACATGTGC ATACTGAACT
-2274 CCATTTCCTT TCCCAAACT TCGACATTTA CAGCCATCCT CTTTCAGCTG ATAGCAAGTT TATCCTTCCA
-2204 GCTACTCAAA CCAGAATCTT TAGAGCCATC CTTGACCCTT TCCCTCCTCT CACACTCAAC ATCTATCCAT
-2134 CAGAAAATTT TGTTGTTCT ACTTTCAAAA TGCATACAGA GTCAGAGCAT GTCTCATTAC CTCCAATAGC
-2064 TACCATACTA GTCTGAACAA ACATCATTTC TCACCTGGGT TATTGAACAA ACATCATTTC TCACCTGGGT TATTGAACAA ACATCATTTC TCACCTGGGT
-1994 TATTGATAGC ATCCTAACGG GTCTTCCTGT TTCTTGGTTC CCCTATATTA GCAACACAGC AGTCAGAGGA
-1924 GTCCTTTTAG AACTCAATCA GATCATGTCA CGTCACTCCT CTACTTAAAA TCCTTCAATG GGTCCCATTA
-1854 CACAAAGAGT ACAAACCAGA GCCCTTACAC TGGTCTACAA GTTCCAACAT TTGACTCCTG TTATCTCTCT
-1784 GACATCATAT TCTAATATTA CTGCTGTTGT CCTTTTGCTC CAGTCACACT GTTTGATTAG TAAATATTTA
-1714 TTAAACAAAG CAATCCTAGT CTCCAAAGAG ATCATAGTTT ATCATAGTTT ATTGGAGGAA ACAAGACCT ATAAATGGTT
-1644 ACACACAGAA GGTAGTGATT ATGGTTCTCC CTCACCTCCC CTCACCTCCC ATCCTAAACT TTGACAGGTG AAACTCCCCT
-1574 GGATGTTGAA GGTTGAGGAA TTTGCCAGGG TTCAGGGTGG TGTTGGAGGA GGCAGGGAGG AAGCAAGGAC
```

FIG. 3C

BglII (-1474)

```
-1504  ATTTCAGGCA GGAAGAACAT TACATGCAAA GATCTAAAGA TATGAATTCAG CAACATATTT ATGAATTAC
-1434  AAGTAAAGTA GAAAGTTCTT GCTAAAACAT CAAAAAATAA AGATTTGTGA TTAGGGGCC AGAATGTGGG
-1364  AGGGAAAGAG AGATACAGTT CACACTTTTA GACAGGAGCC AGATCATGAA ATGTTTCTC TTTGTTTGTT
-1294  TCTTCCTTCA CAGCTTTTGA TATGCTCTTG GAGCAATTTA TTAACCATAT TTTTAATGC ATCTCCTGAA
-1224  CAGAGTCAAA GCAATACTTG GAAAGACTC TGAATTTCCT GATTTAAAGA TACAAAGAA AAATCTGGAG
-1154  TCACAATTAA TTTGAGAAGG TAAAGGAGTG GGTGTGCTAC TGTATCAAAT TTAATTTGTA CAAAATCATC
-1084  ATCTCTAGTA ACATTATTTT TTCTAATCTA CTGCGTTTAG ACTACTTTAG TAAAGCTTGA TCTCCCTGTC
-1014  TATCTAAACA CTGATTCACT TACAGCAAGC TTCAGGCTAG CATTGGTCAT ATTAATACCC AACAAATCA

CAP (-885)
- 944  CAAGGTGTTA GTTGCACATG ATTTGTATA AAAGGTGAAC TGAGATTTCA TTCAGTCTAC AGCTCTTGCC

SD' (-852)                          SD (-823)
- 874  AGGCAAGGCA GCCGACCACA GGTGAGTCTT GGCATCTACC GTTTTCAAGT GTGACAGCTA CTTTTGAAAT
- 804  TACAGATTTG TCAGGACATG GAGGACAAAA CTAGAGCTTC TCACTACTGT TGTGTAGGAA ATTTATGCTT
- 734  GTCAACCTGG CTTGTAAAAT ATGGTTAATA TAACGTAATC ACTGTTAGCA AGTAACTGAC TTTATAGACC
- 664  AATATGCCCTC TCTTCTGAAA TGGTCTTATT TTAAACAAAT GTGAGCAAAA GAAATATTT ATGAGATTCT
```

FIG. 3D

```
-594  AAAAATGAAG ACATAATTTT GTAGTATAGA ATTTTCTTGG CCAGGAATGG TGGCTCATGC TTGTAATCCC
-524  AGCACTTTGG GAGGCCAAGG TCAGAGGATT GCTTGAGCCT GGAAGGTTGA AGATGCAGTG ATTCATGATT
-454  ATACCACTGC ACTCCAGCCT GGGCAACAGA GCAAGACCCT GTCTCAAGAA AAGAAAAGAA TTTTATTTTT
-384  CTTTTCAGAC AAAAATAGAC TTTAAAATAA ACAAATATGA TGATCACAAT TATCAGAGTA
-314  ATTACTTTAT GACAGTCAGC AATAAGATTC TAATCTTTAA ATATTCCTCT GCTTAAATCA TTATATTGGA
-244  GTTTTGATCT ATAATATATT CCCACCCTGA CCCAAAAATT GAAGAAGGAC AAGAAAAAT GTTGTTCCAA
-174  GAAACAAAGA TGTAAGTAAA AAGGCATAAG GAAGGAAAAA AAACTTTTGA AGCAAAAATGT GATTGAGGAG
-104  GATGAGCAGA CCAATTATTT TTGGTTTGGT CAGCTTACAT AATGATTATC GTTCTTTGGT TTCTCAGTTT
                                     SA (-5)ATG (1)
 -34  CTAGTGGGCT TCATTGTTTG CTTCCCAGAC CAGGATGAAG ACACTCCAGT TTTTCTTCCT TTTCTGTTGC
                mature (49)                       1▶MetLys ThrLeuGlnP hePhePheLe uPheCysCys
  37  TGGAAAGCAA TCTGCTGCAA TAGCTGTGAG CTGACCAACA TCACCATTGC AATAGAGAAA GAAGAATGTC
     13▶TrpLysAl aI leCysCysAs nSerCysGlu LeuThrAsnI leThrI leAl aI leGluLys GluGluCysA
 107  GTTTCTGCAT AAGCATCAAC ACCACTTGGT GTGCTGGCTA CTGCTACACC AGGTAGGTA CC (SEQ ID NO: 2)
     36▶rgPheCysII eSerIleAsn ThrThrTrpC ysAlaGlyTy rCysTyrThr Arg (SEQ ID NO: 1)
                                                             KpnI (163)
                                                       SD (160)
```

FIG. 3E

```
GGATCCGAGAACATAGAAGGAGCAGGTAATTTATCAAGGCATGAACACGGGTGCTTAATTTCCTA
TTTTGAGGCCAGGCATGGTGGCTCACACCTGTAATCCCAACACTTTAGGAAGCCAAGGTGGGTGG
ATTGCTTGAGTCTAGGATTTTGAGACCAGCCTGGCCAACATGGCGAAATCCTGTCTCTACTAAAA
ATACTAAAATTAACCAGTCATGGTGGTGGTGTGCCTTTAGTCCCAGCTACTCTGGTGGCTGAGGC
ACAAGAATCACTTGAACCTGGGAGGCAGAGGTTGCAGTGAGCTGAGACTGTGCCACTTCACTCCA
GCCTGGGTGACAGAGTAAGATTCTGTCTCAAAAAATATGTATATATACACACATATAATAGATAC
ATAAACATATATACATATATAATATATAAATATATATATTATATATAATATATAAACATATATAA
ATATATATATATATATATATATATATATAAACCAAACATAAAGGAATAATTTTGGGGGAAAAT
CTTCATAAATGAAAGAACAACATAGGCTGTTGAGTATATGCACAGAAATTCAAGAGATCTTCCAG
CAATTGAAGACATTGGTTTACCAGAATTCACAAAAGAAGTCAGCTGTGCATTTAAAGTAGAATGT
GATGAGTGTTACCACTGAGGTAGGAACTGGGAACTAAGGAAGCGTAAGACAGAAAGTGCTGAACT
GAGAGTTGGGCATTGGAGGCTGTGTAAGGCAGGGTAAGTGAATGTCTCCTAGAAGCTACCTTTAA
ATGGAGTTTTGAAGTACTTGTAGGAGTAGCTTAGGTGAAAAGAAGAGGAGAAACATGTATCAGGC
AGAGGGACTAGAACCTTATTACCTTCAAAGAAGAAGCAAAAAGAATACATGTGACTTTGAGGTGG
TGGGAGGTGCTTTAAGCCAATATAGGTGAATTTGACATAGGACTTCCCTAAATAATGTTCGGTCA
TTTGTTAAATATTGAGTGATATATCACTGTATTAAAGCCCAAGAGTTGCTTTTATATAGAAAGAA
GAAAAAAGCCCAAGAGAGTTTTATTTCTAGAGGGAATATTTTCTAGAAATAAAGGAAGGTGTATC
AGCCAGTTTCTAGTCAGGAAAACAGAAATCACACCTGATATGCAAAATAGAGGAAAATCAGGGAA
TTCATTAATCCAGAGATTTGGTTGCTCAAGTATTAGATTGCTGAAAAGCCAGACAGGGAATATGA
GGCAATCAGAGATAAGTATTAGTGACAAGCTCCATTTATGTGCAGGATTGGAGGGACATAGGTGG
GGTTCCCAGAAGCCAGAAGGTGAGACCACCTAGCAGAAGCTCAAACCACAGCTGGGGTTTCCTCA
CAAAAGCTGGGACCACCAGGAGGAGCTGTCCAATGGGATCTGGAGCCAGGGAGATCATGCAGTCA
CTACCAGGAAGGGAAGCAGAATGTAAAAGGTAGAGAGAAATACTCCAACTGCTTCCTTGCATTCA
CTTTCCAATCTCCATTCACAAAGGCAAAAACCTGCTAATACAGCAGAGTGGGAAAAGCAGCCTGC
CAAGGTCCTTTCTCCCACAAAACAGAGCACAAAACCAAGCAAAAACAAGGAATGCATTTGATAGC
AAACAGGCTATGGACCAACCCAACATAAAAGAAATGATGAGTGATTTCTTTTTTCATTTGGTTCA
AGAAAAGTATTTCAGTAACTATTATGTAACAGAAATTCTATTTATTTTGGGGAATTCAAAGGTGA
ATAAAAAAGAACTCTAAATTTTTATCAATAAAATATTTCAAAAACCTCAATGAGAGTAATGGCAT
TAACTAGCAAATATGCTAATGAGATGAGCTAGCCATAAGAGGCTTAGAATTGAGAGAAAGGTCTG
GGGGCCTCTTGACAGGCCAAATTCAGAGCTGTTTGTGGGAATCTCTGACCTAACTGCAGGTGGAA
ATATAAATATGGGCATTTAGAATAGTGGCCCAAACTTTGGATGATTTCTGTCTTGGGGTCTCTCC
AATTAATGGGATTGATGAGAACTGTAGACCACTGAGGTCACCATGGCTCAATGAATAGTCCCCTG
GCTTTGGAGTCAAACTGACCTGAATATGAACCCCAGCTTTGCTACTTACAGGTTGCATTTATCCT
CAGTTTTCTCATCTTTCAAAGAAGAACAGTAACTTCTTTAAAAGGTTATTGTAGGCTGGGTGCAG
TGGCTCACGCCTGTAATCGCAGCACTTTGGGAGGCGGAGGCTAGTGGATCACTTGAGGCCAGGAG
TTGGAAACTAGCCTGGCCAACATGGTGAAACTCTGTCTCTACAAAAGAAATTTAAAAAATTTTG
CTGGGTGTGGTGGCACACACCTGGAATTCCAGCTACCTGGGAGGCCGAGGCATGAGCATCACTTG
AGTCTGGAAGCAGAGGGTTGCAGTGAGCCAAGATTGTACCACTGTACTCAAGCCTGGGTGACAC
AGTGAGACCTTGTCTAAAAAAAAAAAAAGGTTATTGTGTTATTGTAAATATTGTATATGAACTTCT
ATTTAACATGTTTAGTTAAATGCCTGTGTAATTGTCCAATGTGCTCTTCTAGCTCACTGCACAGA
CAAAACTGATTCACTGAAATCATGGAATTGCAGCAAAGAACAAATCTAATTAATGTAGGTCAAAC
GGGAGGACTGGAGTTATTATTCAAATCAGTCTCCCTGAAAACTCAGAGGCTAGGGTTTTATGGAT
AATTTGGTGGGCAGGGACTAGGGAATGGGTGCTGCTGATTGGTTGGGAATGAAATAGTAAGAT
TGTGGAAAACTGTCCTCCTTCATTGAGTCTGCTTCCGGGTGTAGGCCACACGACCAGTTGAGTCA
TGAAGCATGCGTCCAAGTGGAGTCAGTTTGTTGCCAGAATGCAAAGCCTGAAAATGTCTCAAA
TGATCAACTGTAGGCTCCACAATAATGATATTATCTATAGGAGCAATTGGGAAGTAACAAATCT
TGTGACCTCTGGACACATAACTCCTGAACTAGTAAGGGATTATAAAACCATGCCTATATCTTAT
CAGAATTCAGGTCCCCCCATAATCCTAATCTCACAGCATTTCATTGTTTAGAAAGGCCATTTTC
AGTCCCTGAGCAAGGAGGGGGTTAGTTTTAGGATAGGACTATTATCCTTGCTTCGTTAAACTATA
```

FIG. 9A

```
AACTAAATTCCTCCCATGGTTAGCTTGGCCTACACCTAAGAATGAGTGAGAACAGCCAGCCTGTG
AGGCTAGAGGCAAGATGGAGTCAGCCATGCTAGATTTATCTCACTGTCATAACCTTTGCAAAGGC
AGTTTCACCTGGGACATAGGAGGTACTCAATGAAAAGAAGCTATTAATATTAAAATTTTAAAAA
TGAATTTAAGGAACTAATACTATGTACATATTAGTCATTAAAACAAAGTGGTTCATTTACATTCA
CACAAATAAATCTTGTGATTATACATAGGTAATATGAAAAACTTTGTTTTCTTTCATAATACAAG
GTATTAGCAATAGATATAGTAATGTTAGCATTCCTTTGGAAAAAATGAAAGATTTATAATTTTC
CAAGAATCATTAGTATTTTTATTTAATATACATAATATAAAATTTATTCATTCTATAACTTGGAA
ATATGCTTGCTTACCAATTACTGACAGATTTCAAAATATTTCTATACTCACAATATTCATTTACA
TAAATATTGATTTGGTACTTACAATGTGTACTGCTATGCTAAGTTTTGTCTTTGTCAAACATATT
TTATAAAATCATAATCCTAGATGAATCCAACTTTTGGTAACCCACGTGCCTGAACCCCTGCTGTT
AACAGGCAAAGTGTGGTAGGTACAGATCTATACCTACCACCTTCCTCTACCCACCAGCATCTGCA
CCCACCACCCCTCCCCACCCACCATTATCTATACCAACCACCCCTCCCAACCTACCAGCATCTGC
ACCCACCACACCGCCCACCCACCACCATGTACACTCACTACACCTTCCAGCCATCACCATCTGCA
CCCATCACTCCTCCCCATCCACAAGCATCTGCACCCACCACATTTCCCTACCTACCAGCATCTTC
ACTCACCACCTCTCCACCCACCAGCATCTGCACCCACAACCCCTCCTCACCCACCAGAGTCTGCA
TCCATCACACTTGCCCACTCGCTAGCATCTGCACCATCAAGCTCTGCCTTCTTGCCTAATACGGG
ATGAGCTCTCCATGGTTCTGCCTAAAGACAATGCTTCCACTCCTCTTCTATAACCCATTTCCTTT
TACCTCTTCAAGTACACTTCAGAACTTCTCTCTCCTTCTGATACCAACTTTTTCCACTTTACTCA
ATCATTCCTATCACCATACAAACGTGTTTATTTCTCCCATCTTAAAGTTAAAAATCAAAAGAAAA
TTGTCTGCGGCCAGGCACGGTGGCTCACGCCTGTAATCCCAACACTTTGGGAGGCCAAGGAGGGT
TGGATGACTTAAGGTTAGGAGTTCAAGACCAGCCTGGCCAACATGGTGAAACCCATCTCTACTAA
AAATACAAAAATTAGCCAGGCATGGTGGCACATGCCTGTAGTCTCAGGTACTTGGGAGGCTGAGG
CCAGAGAATGGCTTGAACCCGGGAGGCAGAGGTTGCAGTGAGCCGAGATTGTGCCCTTGCACTCC
AGCCTGGGTGACAGAGTGAGACTCCATCTCAAAAATAAAAATAAAAATAAAACAAAAGAAAGTT
ATTTTTACCCAACATCCACATTAACCAAATACCCATTTCTTTATTGATCTTTGTAAAAAAAGCT
CTTGGAAAAATTGTCTATATTCACTATGACTTATCTCCTCCAAATCACTTAAACACATACCAATC
AGGTTTTTGTTTTCATCATTCCAAAGTAACTTTTACAGCCAAGGACAGTAGCGAACTTTACATCG
CATATGCATTGTGAAGTTCTTGATCCTCATCTTACTTAACCTGTCAGCAGTATCTGACACAGGTG
TCACTGGCTCCTCCCTGAGATGCTCTCTTTATTTGGCTTTGGGACACCATATTCTCCCCATTCC
TACTTTCCTCAATGGCCCTCCTCAGTCTCCTTTGGAAAGAGGAAAAGAAACTTCATTATCTCCT
GGATGTAGTACAAACAACTCAAGCTCAACATGTGCATACTGAACTCCATTTCCTTTTCCCAAACT
TCGACATTTACAGCCATCCCCTTTCAGCTGATAGCAAGTTTATCCTTCCAGCTACTCAAACCAGA
ATCTTTAGAGCCATCCTTGACCCTTTTCCTCCTCTCACACTCAACATCTATCCATCAGAAAATTT
TGTTGGTTCTACTTTCAAAATGCATACAGAGTCAGAGCATGTCTCATTACCTCCAATAGCTACCA
TACTAGTCTGAACAAACATCATTTCTCACCTGGGTTATTGAACAAACATCATTTCTCACCTGGGT
TATTGATAGCATCCTAACGGGTCTTCCTGTTTCTTGGTTCCCTATATTAGCAACACAGCAGTCA
GAGGAGTCCTTTTAGAACTCAATCAGATCATGTCACGTCACTCCTCTACTTAAAATCCTTCAATG
GGTCCCATTACACAAAGAGTACAAACCAGAGCCCTTACACTGGTCTACAAGTTCCAACATTTGAC
TCCTGTTATCTCTCTGACATCATATTCTAATATTACTGCTGTTGTCCTTTTGCTCCAGTCACACT
GTTTGATTAGTAAATATTTATTAAACAAAGCAATCCTAGTCTCCAAAGAGATCATAGTTTATTGG
AGGAAACAAGAGCCTATAAATGGTTACACACAGAAGGTAGTGATTATGGTTCTCCCTCACCTCCC
ATCCTAAACTTTGACAGGTGAAACTCCCCTGGATGTTGAAGGTTGAGGAATTTGCCAGGGTTCAG
GGTGGTGTTGGAGGAGGCAGGGAGGAAGCAAGGACATTTCAGGCAGGAAGAACATTACATGCAAA
GATCTAAAGATATGAATCAGCAACATATTTATGGAATTACAAGTAAAGTAGAAAGTTC
```

FIG. 9B

```
TCACTGTTAGCAAGTAACTGACTTTATAGACCAATATGCCTCTCTTCTGAAATGGTCTTATTTTA
AACAAATGTGAGCAAAAGAAAATATTTATGAGATTCTAAAAATGAAGACATAATTTTGTAGTATA
GAATTTTCTTGGCCAGGAATGGTGGCTCATGCTTGTAATCCCAGCACTTTGGGAGGCCAAGGTCA
GAGGATTGCTTGAGCCTGGAAGGTTGAAGATGCAGTGATTCATGATTATACCACTGCACTCCAGC
CTGGGCAACAGAGCAAGACCCTGTCTCAAGAAAAGAAAAGAATTTTATTTTTCTTTTCAGACAAA
AATAGACTTTAAAATAATAATGGAAGAACAAATATGATGATCACAATTATCAGAGTAATTACTTT
ATGACAGTCAGCAATAAGATTCTAATCTTTAAATATTCCTCTGCTTAAATCATTATATTGGAGTT
TTGATCTATAATATATTCCCACCCTGACCCAAAAATTGAAGAAGGACAAGGAAAAATGTTGTTCC
AAGAAACAAAGATGTAAGTAAA
```

FIG. 10

```
      E
      G ATCTATACCT ACCACCTTCC TCTACCCACC AGCATCTGCA CCCACCACCC CTCCCCACCC
ACCATTATCT ATACCAACCA CCCCTCCCAA CCTACCAGCA TCTGCACCCA CCACACCGCC CACCCACCAC
CATGTACACT CACTACACCT TCCAGCCATC ACCATCTGCA CCCATCACTC CTCCCCATCC ACAAGCATCT
GCACCCACCA CATTTCCCTA CCTACCAGCA TCTTCACTCA CCACCTCTCC ACCCACCAGC ATCTGCACCC
ACAACCCCTC CTCACCCACC AGAGTCTGCA TCCATCACAC TTGCCCACTC GCTAGCATCT GCACCATCAA
GCTCTGCCTT CTTGCCTAAT ACGGGATGAG CTCTCCATGG TTCTGCCTAA AGACAATGCT TCCACTCCTC
TTCTATAACC CATTTCCTTT TACCTCTTCA AGTACACTTC AGAACTTCTC TCTCCTTCTG ATACCAACTT
TTTCCACTTT ACTCAATCAT TCCTATCACC ATACAAACGT GTTTATTTCT CCCATCTTAA AGTTAAAAAT
CAAAAGAAAA TTGTCTGCGG CCAGGCACGG TGGCTCACGC CTGTAATCCC AACACTTTGG GAGGCCAAGG
AGGGTTGGAT GACTTAAGGT TAGGAGTTCA AGACCAGCCT GGCCAACATG GTGAAACCCA TCTCTACTAA
AAATACAAAA ATTAGCCAGG CATGGTGGCA CATGCCTGTA GTCTCAGGTA CTTGGGAGGC TGAGGCCAGA
           Smal
GAATGGCTTG AACCCGGGAG GCAGAGGTTG CAGTGAGCCG AGATTGTGCC CTTGCACTCC AGCCTGGGTG
ACAGAGTGAG ACTCCATCTC AAAAATAAAA AATAAAAATA AAACAAAGA AAGTTATTTT TACCCAACAT
CCACATTAAC CAAATACCCA TTTCTTTATT GATCTTTGTA AAAAAAGCT CTTGGAAAAA TTGTCTATAT
TCACTATGAC TTATCTCCTC CAAATCACTT AAACACATAC CAATCAGGTT TTTGTTTTCA TCATTCCAAA
                                          Ndel                  BsaBI
GTAACTTTTA CAGCCAAGGA CAGTAGCGAA CTTTACATCG CATATGCATT GTGAAGTTCT TGATCCTCAT
CTTACTTAAC CTGTCAGCAG TATCTGACAC AGGTGTCACT GGCTCCTCCC TGAGATGCTC TCTTTATTTG
GCTTTGGGGA CACCATATTC TCCCCATTCC TACTTTCCTC AATGGCCCTC CTCAGTCTCC TTTGGAAAGA
GGAAAAAGAA ACTTCATTAT CTCCTGGATG TAGTACAAAC AACTCAAGCT CAACATGTGC ATACTGAACT
CCATTTCCTT TTCCCAAACT TCGACATTTA CAGCCATCCC CTTTCAGCTG ATAGCAAGTT TATCCTTCCA
GCTACTCAAA CCAGAATCTT TAGAGCCATC CTTGACCCTT TTCCTCCTCT CACACTCAAC ATCTATCCAT
CAGAAAATTT TGTTGGTTCT ACTTTCAAAA TGCATACAGA GTCAGAGCAT GTCTCATTAC CTCCAATAGC
TACCATACTA GTCTGAACAA ACATCATTTC TCACCTGGGT TATTGAACAA ACATCATTTC TCACCTGGGT
TATTGATAGC ATCCTAACGG GTCTTCCTGT TTCTTGGTTC CCTATATTA GCAACACAGC AGTCAGAGGA
GTCCTTTTAG AACTCAATCA GATCATGTCA CGTCACTCCT CTACTTAAAA TCCTTCAATG GGTCCCATTA
CACAAAGAGT ACAAACCAGA GCCCTTACAC TGGTCTACAA GTTCCAACAT TTGACTCCTG TTATCTCTCT
GACATCATAT TCTAATATTA CTGCTGTTGT CCTTTTGCTC CAGTCACACT GTTTGATTAG TAAATATTTA
TTAAACAAAG CAATCCTAGT CTCCAAAGAG ATCATAGTTT ATTGGAGGAA ACAAGAGCCT ATAAATGGTT
ACACACAGAA GGTAGTGATT ATGGTTCTCC CTCACCTCCC ATCCTAAACT TGACAGGTG AAACTCCCCT
GGATGTTGAA GGTTGAGGAA TTTGCCAGGG TTCAGGGTGG TGTTGGAGGA GGCAGGGAGG AAGCAAGGAC
                     BgIII
ATTTCAGGCA GGAAGAACAT TACATGCAAA GATC
```

FIG. 11

```
                                            TC ACTGTTAGCA AGTAACTGAC TTTATAGACC
AATATGCCTC TCTTCTGAAA TGGTCTTATT TTAAACAAAT GTGAGCAAAA GAAAATATTT ATGAGATTCT
AAAAATGAAG ACATAATTTT GTAGTATAGA ATTTTCTTGG CCAGGAATGG TGGCTCATGC TTGTAATCCC
AGCACTTTGG GAGGCCAAGG TCAGAGGATT GCTTGAGCCT GGAAGGTTGA AGATGCAGTG ATTCATGATT
ATACCACTGC ACTCCAGCCT GGGCAACAGA GCAAGACCCT GTCTCAAGAA AAGAAAAGAA TTTTATTTTT
CTTTTCAGAC AAAAATAGAC TTTAAAATAA TAATGGAAGA ACAAATATGA TGATCACAAT TATCAGAGTA
                        BsaBI
ATTACTTTAT GACAGTCAGC AATAAGATTC TAATCTTTAA ATATTCCTCT GCTTAAATCA TTATATTGGA
GTTTTGATCT ATAATATATT CCCACCCTGA CCCAAAAATT GAAGAAGGAC AAGGAAAAAT GTTGTTCCAA
GAAACAAAGA TGTAAGTAAA
```

FIG. 12

SEQUENCE LISTING

<160> NUMBER OF SEQ ID NOS: 7

<210> SEQ ID NO 1
<211> LENGTH: 7622
<212> TYPE: DNA
<213> ORGANISM: Homo sapiens

<400> SEQUENCE: 1

```
ggatccgaga acatagaagg agcaggtaat ttatcaaggc atgaacacgg gtgcttaatt          60
tcctattttg aggccaggca tggtggctca cacctgtaat cccaacactt taggaagcca         120
aggtgggtgg attgcttgag tctaggattt tgagaccagc ctggccaaca tggcgaaatc         180
ctgtctctac taaaaatact aaaattaacc agtcatggtg gtggtgtgcc tttagtccca         240
gctactctgg tggctgaggc acaagaatca cttgaacctg ggaggcagag gttgcagtga         300
gctgagactg tgccacttca ctccagcctg ggtgacagag taagattctg tctcaaaaaa         360
tatgtatata tacacacata taatagatac ataaacatat atacatatat aatatataaa         420
tatatatatt atatataata tataaacata tataaatata tatatatata tatatatata         480
tatataaacc aaacataaag gaataatttt gggggaaaat cttcataaat gaaagaacaa         540
cataggctgt tgagtatatg cacagaaatt caagagatct tccagcaatt gaagacattg         600
gtttaccaga attcacaaaa gaagtcagct gtgcatttaa agtagaatgt gatgagtgtt         660
accactgagg taggaactgg gaactaagga agcgtaagac agaaagtgct gaactgagag         720
ttgggcattg gaggctgtgt aaggcagggt aagtgaatgt ctcctagaag ctacctttaa         780
atggagtttt gaagtacttg taggagtagc ttaggtgaaa agaagaggag aaacatgtat         840
caggcagagg gactagaacc ttattacctt caaagaagaa gcaaaaagaa tacatgtgac         900
tttgaggtgg tgggaggtgc tttaagccaa tataggtgaa tttgacatag gacttcccta         960
aataatgttc ggtcatttgt taaatattga gtgatatatc actgtattaa agcccaagag        1020
ttgcttttat atagaaagaa gaaaaaagcc caagagagtt ttatttctag agggaatatt        1080
ttctagaaat aaaggaaggt gtatcagcca gtttctagtc aggaaaacag aaatcacacc        1140
tgatatgcaa aatagaggaa aatcagggaa ttcattaatc cagagatttg gttgctcaag        1200
tattagattg ctgaaaagcc agacagggaa tatgaggcaa tcagagataa gtattagtga        1260
caagctccat ttatgtgcag gattggaggg acataggtgg ggttcccaga agccagaagg        1320
```

```
tgagaccacc tagcagaagc tcaaaccaca gctggggttt cctcacaaaa gctgggacca    1380
ccaggaggag ctgtccaatg ggatctggag ccagggagat catgcagtca ctaccaggaa    1440
gggaagcaga atgtaaaagg tagagagaaa tactccaact gcttccttgc attcactttc    1500
caatctccat tcacaaaggc aaaaacctgc taatacagca gagtgggaaa agcagcctgc    1560
caaggtcctt tctcccacaa aacagagcac aaaaccaagc aaaaacaagg aatgcatttg    1620
atagcaaaca ggctatggac caacccaaca taaaagaaat gatgagtgat ttcttttttc    1680
atttggttca agaaaagtat ttcagtaact attatgtaac agaaattcta tttattttgg    1740
ggaattcaaa ggtgaataaa aaagaactct aaattttat caataaaata tttcaaaaac    1800
ctcaatgaga gtaatggcat taactagcaa atatgctaat gagatgagct agccataaga    1860
ggcttagaat tgagagaaag gtctggggc ctcttgacag gccaaattca gagctgtttg     1920
tgggaatctc tgacctaact gcaggtgaaa atataaatat gggcatttag aatagtggcc    1980
caaactttgg atgatttctg tcttggggtc tctccaatta atgggattga tgagaactgt    2040
agaccactga ggtcaccatg gctcaatgaa tagtcccctg gctttggagt caaactgacc    2100
tgaatatgaa ccccagcttt gctacttaca ggttgcattt atcctcagtt ttctcatctt    2160
tcaaagaaga acagtaactt ctttaaaagg ttattgtagg ctgggtgcag tggctcacgc    2220
ctgtaatcgc agcactttgg gaggcggagg ctagtggatc acttgaggcc aggagttgga    2280
aactagcctg gccaacatgg tgaaactctg tctctacaaa aagaaattta aaaattttg     2340 ctgggtgtgg tggcacacac ctggaattcc agctacctgg gaggccgagg catgagcatc    2400
acttgagtct ggaaagcaga gggttgcagt gagccaagat tgtaccactg tactcaagcc    2460
tgggtgacac agtgagacct tgtctaaaaa aaaaaaggt tattgtgtta ttgtaaatat     2520
tgtatatgaa cttctatta acatgtttag ttaaatgcct gtgtaattgt ccaatgtgct    2580
cttctagctc actgcacaga caaaactgat tcactgaaat catggaattg cagcaaagaa    2640
caaatctaat taatgtaggt caaacgggag gactggagtt attattcaaa tcagtctccc    2700
tgaaaactca gaggctaggg ttttatggat aatttggtgg gcaggggact agggaatggg    2760
tgctgctgat tggttgggga atgaaatagt aagattgtgg aaaactgtcc tccttcattg    2820
agtctgcttc cgggtgtagg ccacacgacc agttgagtca tgaagcatgc gtccaagtgg    2880
agtcagtttg ttgccagaat gcaaaagcct gaaaaatgtc tcaaatgatc aactgtaggc    2940
tccacaataa tgatattatc tataggagca attggggaag taacaaatct tgtgacctct    3000
ggacacataa ctcctgaact agtaagggat tataaaaacc atgcctatat cttatcagaa    3060
ttcaggtccc cccataatcc taatctcaca gcatttcatt tgtttagaaa ggccattttc    3120
agtccctgag caaggagggg gttagtttta ggataggact attatccttg cttcgttaaa    3180
ctataaacta aattcctccc atggttagct tggcctacac ctaagaatga gtgagaacag    3240
ccagcctgtg aggctagagg caagatggag tcagccatgc tagatttatc tcactgtcat    3300
aacctttgca aggcagttt cacctgggac ataggaggta ctcaatgaaa agaagctat     3360 taatattaaa attttaaaaa tgaatttaag gaactaatac tatgtacata ttagtcatta    3420
aaacaaagtg gttcatttac attcacacaa ataaatcttg tgattataca taggtaatat    3480
gaaaaacttt gttttctttc ataatacaag gtattagcaa tagatatagt aatgttagca    3540 ttccttttgga aaaaatgaaa agatttataa ttttccaaga atcattagta tttttattta   3600
atatacataa tataaaattt attcattcta taacttggaa atatgcttgc ttaccaatta    3660
```

```
ctgacagatt tcaaaatatt tctatactca caatattcat ttacataaat attgatttgg    3720
tacttacaat gtgtactgct atgctaagtt ttgtctttgt caaacatatt ttataaaatc    3780
ataatcctag atgaatccaa cttttggtaa cccacgtgcc tgaaccctg ctgttaacag     3840 gcaaagtgtg gtaggtacag atctatacct accaccttcc tctacccacc agcatctgca    3900
cccaccaccc ctccccaccc accattatct ataccaacca ccctcccaa cctaccagca     3960 tctgcaccca ccacaccgcc cacccaccac catgtacact cactacacct tccagccatc    4020
accatctgca cccatcactc ctccccatcc acaagcatct gcaccacca catttcccta     4080 cctaccagca tcttcactca ccacctctcc acccaccagc atctgcaccc acaacccctc    4140
ctcacccacc agagtctgca tccatcacac ttgcccactc gctagcatct gcaccatcaa    4200
gctctgcctt cttgcctaat acgggatgag ctctccatgg ttctgcctaa agacaatgct    4260
tccactcctc ttctataacc catttccttt tacctcttca agtacacttc agaacttctc    4320
tctccttctg ataccaactt ttttccacttt actcaatcat tcctatcacc atacaaacgt    4380
gtttatttct cccatcttaa agttaaaaat caaaagaaaa ttgtctgcgg ccaggcacgg    4440
tggctcacgc ctgtaatccc aacactttgg gaggccaagg agggttggat gacttaaggt    4500
taggagttca agaccagcct ggccaacatg gtgaaaccca tctctactaa aaatacaaaa    4560
attagccagg catggtggca catgcctgta gtctcaggta cttgggaggc tgaggccaga    4620
gaatggcttg aacccgggag gcagaggttg cagtgagccg agattgtgcc cttgcactcc    4680
agcctgggtg acagagtgag actccatctc aaaaataaaa aataaaaata aacaaaaga    4740 aagttatttt tacccaacat ccacattaac caaatcccca tttctttatt gatctttgta    4800
aaaaaaagct cttggaaaaa ttgtctatat tcactatgac ttatctcctc caaatcactt    4860
aaacacatac caatcaggtt tttgttttca tcattccaaa gtaacttta cagccaagga     4920 cagtagcgaa ctttacatcg catatgcatt gtgaagttct tgatcctcat cttacttaac    4980
ctgtcagcag tatctgacac aggtgtcact ggctcctccc tgagatgctc tctttatttg    5040
gctttgggga caccatattc tccccattcc tactttcctc aatggccctc ctcagtctcc    5100
tttggaaaga ggaaaaagaa acttcattat ctcctggatg tagtacaaac aactcaagct    5160
caacatgtgc atactgaact ccatttcctt ttcccaaact tcgacattta cagccatccc    5220 cttttcagctg atagcaagtt tatccttcca gctactcaaa ccagaatctt tagagccatc    5280
cttgacccct ttcctcctct cacactcaac atctatccat cagaaaattt tgttggttct    5340
actttcaaaa tgcatacaga gtcagagcat gtctcattac ctccaatagc taccatacta    5400
gtctgaacaa acatcatttc tcacctgggt tattgaacaa acatcatttc tcacctgggt    5460
tattgatagc atcctaacgg gtcttcctgt ttcttggttc ccctatatta gcaacacagc    5520
agtcagagga gtcctttag aactcaatca gatcatgtca cgtcactcct ctacttaaaa     5580
tccttcaatg ggtcccatta cacaaagagt acaaaccaga gcccttacac tggtctacaa    5640
gttccaacat ttgactcctg ttatctctct gacatcatat tctaatatta ctgctgttgt    5700 cctttttgctc cagtcacact gtttgattag taaatattta ttaaacaaag caatcctagt    5760
ctccaaagag atcatagttt attggaggaa acaagagcct ataaatggtt acacacagaa    5820
ggtagtgatt atggttctcc ctcacctccc atcctaaact ttgacaggtg aaactcccct    5880
ggatgttgaa ggttgaggaa tttgccaggg ttcagggtgg tgttggagga ggcagggagg    5940
aagcaaggac atttcaggca ggaagaacat tacatgcaaa gatctaaaga tatgaatcag    6000
caacatattt atggaattac aagtaaagta gaaagttctt gctaaaacat caaaaaataa    6060
```

```
agatttgtga ttaggggccc agaatgtggg agggaaagag agatacagtt cacacttttta    6120
gacaggagcc agatcatgaa atgttttctc tttgtttgtt tcttccttca cagcttttga    6180
tatgctcttg gagcaatttta ttaaccatat tttttaatgc atctcctgaa cagagtcaaa    6240
gcaatacttg gaaaggactc tgaatttcct gatttaaaga tacaaaagaa aaatctggag    6300
tcacaattaa tttgagaagg taaggagtg ggtgtgctac tgtatcaaat ttaatttgta    6360
caaaatcatc atctctagta acattatttt ttctaatcta ctgcgtttag actactttag    6420
taaagcttga tctccctgtc tatctaaaca ctgattcact tacagcaagc ttcaggctag    6480
cattggtcat attaataccc aacaaatcca caaggtgtta gttgcacatg attttgtata    6540
aaaggtgaac tgagatttca ttcagtctac agctcttgcc aggcaaggca gccgaccaca    6600
ggtgagtctt ggcatctacc gttttcaagt gtgacagcta cttttgaaat tacagatttg    6660
tcaggacatg gaggacaaaa ctagagcttc tcactactgt tgtgtaggaa atttatgctt    6720
gtcaacctgg cttgtaaaat atggttaata taacgtaatc actgttagca agtaactgac    6780
tttatagacc aatatgcctc tcttctgaaa tggtcttatt ttaaacaaat gtgagcaaaa    6840
gaaaatattt atgagattct aaaaatgaag acataatttt gtagtataga attttcttgg    6900
ccaggaatgg tggctcatgc ttgtaatccc agcactttgg gaggccaagg tcagaggatt    6960
gcttgagcct ggaaggttga agatgcagtg attcatgatt ataccactgc actccagcct    7020
gggcaacaga gcaagaccct gtctcaagaa aagaaaagaa ttttatttttt cttttcagac    7080
aaaaatagac tttaaaataa taatggaaga acaaatatga tgatcacaat tatcagagta    7140
attactttat gacagtcagc aataagattc taatctttaa atattcctct gcttaaatca    7200
ttatattgga gttttgatct ataatatatt cccaccctga cccaaaaatt gaagaaggac    7260
aaggaaaaat gttgttccaa gaaacaaaga tgtaagtaaa aaggcataag gaaggaaaaa    7320
aaacttttga agcaaaatgt gattgaggag gatgagcaga ccaattattt ttggtttggt    7380
cagcttacat aatgattatc gttctttggt ttctcagttt ctagtgggct tcattgtttg    7440
cttcccagac caggatgaag acactccagt ttttcttcct tttctgttgc tggaaagcaa    7500
tctgctgcaa tagctgtgag ctgaccaaca tcaccattgc aatagagaaa gaagaatgtc    7560
gtttctgcat aagcatcaac accacttggt gtgctggcta ctgctacacc agggtaggta    7620
cc                                                                    7622
```

<210> SEQ ID NO 2
<211> LENGTH: 53
<212> TYPE: PRT
<213> ORGANISM: Homo sapiens

<400> SEQUENCE: 2

Met Lys Thr Leu Gln Phe Phe Phe Leu Phe Cys Cys Trp Lys Ala Ile
1               5                   10                  15
Cys Cys Asn Ser Cys Glu Leu Thr Asn Ile Thr Ile Ala Ile Glu Lys
            20                  25                  30
Glu Glu Cys Arg Phe Cys Ile Ser Ile Asn Thr Thr Trp Cys Ala Gly
        35                  40                  45
Tyr Cys Tyr Thr Arg
    50

<210> SEQ ID NO 3
<211> LENGTH: 40
<212> TYPE: DNA

<210> SEQ ID NO 4
<211> LENGTH: 6038
<212> TYPE: DNA
<213> ORGANISM: Homo sapiens

<400> SEQUENCE: 3
ttggcatcta ccgttttcaa gtggtgacag ctacttttga                                40

<210> SEQ ID NO 4
<211> LENGTH: 6038
<212> TYPE: DNA
<213> ORGANISM: Homo sapiens

<400> SEQUENCE: 4

```
ggatccgaga acatagaagg agcaggtaat ttatcaaggc atgaacacgg gtgcttaatt          60
tcctattttg aggccaggca tggtggctca cacctgtaat cccaacactt taggaagcca         120
aggtgggtgg attgcttgag tctaggattt tgagaccagc ctggccaaca tggcgaaatc         180
ctgtctctac taaaaatact aaaattaacc agtcatggtg gtggtgtgcc tttagtccca         240
gctactctgg tggctgaggc acaagaatca cttgaacctg ggaggcagag gttgcagtga         300
gctgagactg tgccacttca ctccagcctg ggtgacagag taagattctg tctcaaaaaa         360
tatgtatata tacacacata taatagatac ataaacatat atacatatat aatatataaa         420
tatatatatt atataataa tataaacata tataaatata tatatatata tatatatata          480
tatataaacc aaacataaag gaataatttt gggggaaaat cttcataaat gaaagaacaa         540
cataggctgt tgagtatatg cacagaaatt caagagatct tccagcaatt gaagacattg         600
gtttaccaga attcacaaaa gaagtcagct gtgcatttaa agtagaatgt gatgagtgtt         660
accactgagg taggaactgg gaactaagga agcgtaagac agaaagtgct gaactgagag         720
ttgggcattg gaggctgtgt aaggcagggt aagtgaatgt ctcctagaag ctacctttaa         780
atggagtttt gaagtacttg taggagtagc ttaggtgaaa agaagaggag aaacatgtat         840
caggcagagg gactagaacc ttattacctt caaagaagaa gcaaaagaa tacatgtgac          900
tttgaggtgg tgggaggtgc tttaagccaa tataggtgaa tttgacatag gacttcccta         960
aataatgttc ggtcatttgt taaatattga gtgatatatc actgtattaa agcccaagag        1020
ttgcttttat atagaaagaa gaaaaaagcc caagagagtt ttatttctag agggaatatt        1080
ttctagaaat aaaggaaggt gtatcagcca gtttctagtc aggaaaacag aaatcacacc        1140
tgatatgcaa aatagaggaa atcagggaa ttcattaatc cagagatttg gttgctcaag         1200
tattagattg ctgaaaagcc agacaggaa tatgaggcaa tcagagataa gtattagtga         1260
caagctccat ttatgtgcag gattggaggg acataggtgg ggttcccaga agccagaagg        1320
tgagaccacc tagcagaagc tcaaaccaca gctggggttt cctcacaaaa gctgggacca        1380
ccaggaggag ctgtccaatg ggatctggag ccagggagat catgcagtca ctaccaggaa        1440
gggaagcaga atgtaaaagg tagagagaaa tactccaact gcttccttgc attcactttc        1500
caatctccat tcacaaaggc aaaaacctgc taatacagca gagtgggaaa agcagcctgc        1560
caaggtcctt tctcccacaa aacagagcac aaaaccaagc aaaaacaagg aatgcatttg        1620
atagcaaaca ggctatggac caacccaaca taaagaaat gatgagtgat ttcttttttc         1680
atttggttca agaaaagtat ttcagtaact attatgtaac agaaattcta tttattttgg        1740
ggaattcaaa ggtgaataaa aaagaactct aaattttat caataaaata tttcaaaaac         1800
ctcaatgaga gtaatggcat taactagcaa atatgctaat gagatgagct agccataaga        1860
ggcttagaat tgagagaaag gtctgggggc ctcttgacag gccaaattca gagctgtttg        1920
tgggaatctc tgacctaact gcaggtggaa atataaatat gggcatttag aatagtggcc        1980
```

-continued

```
caaactttgg atgatttctg tcttggggtc tctccaatta atgggattga tgagaactgt    2040
agaccactga ggtcaccatg gctcaatgaa tagtcccctg gctttggagt caaactgacc    2100
tgaatatgaa ccccagcttt gctacttaca ggttgcattt atcctcagtt ttctcatctt    2160
tcaaagaaga acagtaactt ctttaaaagg ttattgtagg ctgggtgcag tggctcacgc    2220
ctgtaatcgc agcactttgg gaggcggagg ctagtggatc acttgaggcc aggagttgga    2280
aactagcctg gccaacatgg tgaaactctg tctctacaaa aagaaattta aaaattttg    2340 ctgggtgtgg tggcacacac ctggaattcc agctacctgg gaggccgagg catgagcatc    2400
acttgagtct ggaaagcaga gggttgcagt gagccaagat tgtaccactg tactcaagcc    2460
tgggtgacac agtgagacct tgtctaaaaa aaaaaaggt tattgtgtta ttgtaaatat    2520
tgtatatgaa cttctattta acatgtttag ttaaatgcct gtgtaattgt ccaatgtgct    2580
cttctagctc actgcacaga caaactgat tcactgaaat catggaattg cagcaaagaa    2640
caaatctaat taatgtaggt caaacgggag gactggagtt attattcaaa tcagtctccc    2700
tgaaaactca gaggctaggg ttttatggat aatttggtgg cagggggact agggaatggg    2760
tgctgctgat tggttgggga atgaaatagt aagattgtgg aaaactgtcc tccttcattg    2820
agtctgcttc cgggtgtagg ccacacgacc agttgagtca tgaagcatgc gtccaagtgg    2880
agtcagtttg ttgccagaat gcaaaagcct gaaaaatgtc tcaaatgatc aactgtaggc    2940
tccacaataa tgatattatc tataggagca attggggaag taacaaatct tgtgacctct    3000
ggacacataa ctcctgaact agtaagggat tataaaaacc atgcctatat cttatcagaa    3060
ttcaggtccc cccataatcc taatctcaca gcatttcatt tgtttagaaa ggccattttc    3120
agtccctgag caaggagggg gttagttta ggataggact attatccttg cttcgttaaa    3180
ctataaacta aattcctccc atggttagct tggcctacac ctaagaatga gtgagaacag    3240
ccagcctgtg aggctagagg caagatggag tcagccatgc tagatttatc tcactgtcat    3300
aacctttgca aaggcagttt cacctgggac ataggaggta ctcaatgaaa aagaagctat    3360
taatattaaa atttaaaaa tgaatttaag gaactaatac tatgtacata ttagtcatta    3420
aaacaaagtg gttcatttac attcacacaa ataaatcttg tgattataca taggtaatat    3480
gaaaaacttt gttttctttc ataatacaag gtattagcaa tagatatagt aatgttagca    3540
ttcctttgga aaaatgaaa agatttaaa ttttccaaga atcattagta tttttattta    3600
atatacataa tataaaattt attcattcta taacttggaa atatgcttgc ttaccaatta    3660
ctgacagatt tcaaaatatt tctatactca caatattcat ttacataaat attgatttgg    3720
tacttacaat gtgtactgct atgctaagtt ttgtctttgt caaacatatt ttataaaatc    3780
ataatcctag atgaatccaa cttttggtaa cccacgtgcc tgaacccctg ctgttaacag    3840
gcaaagtgtg gtaggtacag atctatacct accaccttcc tctacccacc agcatctgca    3900
cccaccaccc ctccccaccc accattatct ataccaacca cccctcccaa cctaccagca    3960
tctgcaccca ccacaccgcc cacccaccac catgtacact cactacacct tccagccatc    4020
accatctgca cccatcactc ctccccatcc acaagcatct gcacccacca catttcccta    4080
cctaccagca tcttcactca ccacctctcc acccaccagc atctgcaccc acaacccctc    4140
ctcacccacc agagtctgca tccatcacac ttgcccactc gctagcatct gcaccatcaa    4200
gctctgcctt cttgcctaat acgggatgag ctctccatgg ttctgcctaa agacaatgct    4260
tccactcctc ttctataacc catttccttt tacctcttca agtacacttc agaacttctc    4320
```

-continued

| | |
|---|---|
| tctccttctg ataccaactt tttccacttt actcaatcat tcctatcacc atacaaacgt | 4380 |
| gtttatttct cccatcttaa agttaaaaat caaaagaaaa ttgtctgcgg ccaggcacgg | 4440 |
| tggctcacgc ctgtaatccc aacactttgg gaggccaagg agggttggat gacttaaggt | 4500 |
| taggagttca agaccagcct ggccaacatg gtgaaaccca tctctactaa aaatacaaaa | 4560 |
| attagccagg catggtggca catgcctgta gtctcaggta cttgggaggc tgaggccaga | 4620 |
| gaatggcttg aacccgggag gcagaggttg cagtgagccg agattgtgcc cttgcactcc | 4680 |
| agcctgggtg acagagtgag actccatctc aaaaataaaa aataaaaata aacaaaaga | 4740 |
| aagttatttt tacccaacat ccacattaac caaatacccca tttctttatt gatctttgta | 4800 |
| aaaaaaagct cttggaaaaa ttgtctatat tcactatgac ttatctcctc caaatcactt | 4860 |
| aaacacatac caatcaggtt tttgttttca tcattccaaa gtaacttta cagccaagga | 4920 |
| cagtagcgaa ctttacatcg catatgcatt gtgaagttct tgatcctcat cttacttaac | 4980 |
| ctgtcagcag tatctgacac aggtgtcact ggctcctccc tgagatgctc tctttatttg | 5040 |
| gctttgggga caccatattc tccccattcc tactttcctc aatggccctc ctcagtctcc | 5100 |
| tttggaaaga ggaaaaagaa acttcattat ctcctggatg tagtacaaac aactcaagct | 5160 |
| caacatgtgc atactgaact ccatttcctt ttcccaaact tcgacattta cagccatccc | 5220 |
| ctttcagctg atagcaagtt tatccttcca gctactcaaa ccagaatctt tagagccatc | 5280 |
| cttgacccctt ttcctcctct cacactcaac atctatccat cagaaaattt tgttggttct | 5340 |
| actttcaaaa tgcatacaga gtcagagcat gtctcattac ctccaatagc taccatacta | 5400 |
| gtctgaacaa acatcatttc tcacctgggt tattgaacaa acatcatttc tcacctgggt | 5460 |
| tattgatagc atcctaacgg gtcttcctgt ttcttggttc ccctatatta gcaacacagc | 5520 |
| agtcagagga gtccttttag aactcaatca gatcatgtca cgtcactcct ctacttaaaa | 5580 |
| tccttcaatg ggtcccatta cacaaagagt acaaaccaga gcccttacac tggtctacaa | 5640 |
| gttccaacat ttgactcctg ttatctctct gacatcatat tctaatatta ctgctgttgt | 5700 |
| cctttttgctc cagtcacact gttttgattag taaatattta ttaaacaaag caatcctagt | 5760 |
| ctccaaagag atcatagttt attggaggaa acaagagcct ataaatggtt acacacagaa | 5820 |
| ggtagtgatt atggttctcc ctcacctccc atcctaaact ttgacaggtg aaactcccct | 5880 |
| ggatgttgaa ggttgaggaa tttgccaggg ttcagggtgg tgttggagga ggcagggagg | 5940 |
| aagcaaggac atttcaggca ggaagaacat tacatgcaaa gatctaaaga tatgaatcag | 6000 |
| caacatattt atggaattac aagtaaagta gaaagttc | 6038 |

<210> SEQ ID NO 5
<211> LENGTH: 542
<212> TYPE: DNA
<213> ORGANISM: Homo sapiens

<400> SEQUENCE: 5

| | |
|---|---|
| tcactgttag caagtaactg actttataga ccaatatgcc tctcttctga aatggtctta | 60 |
| ttttaaacaa atgtgagcaa agaaaatat ttatgagatt ctaaaaatga agacataatt | 120 |
| ttgtagtata gaattttctt ggccaggaat ggtggctcat gcttgtaatc ccagcacttt | 180 |
| gggaggccaa ggtcagagga ttgcttgagc ctggaaggtt gaagatgcag tgattcatga | 240 |
| ttataccact gcactccagc ctgggcaaca gagcaagacc ctgtctcaag aaagaaaag | 300 |
| aattttattt ttcttttcag acaaaatag actttaaaat aataatggaa gaacaaatat | 360 |
| gatgatcaca attatcagag taattacttt atgacagtca gcaataagat tctaatctttt | 420 |

| | |
|---|---|
| aaatattcct ctgcttaaat cattatattg gagttttgat ctataatata ttcccaccct | 480 |
| gacccaaaaa ttgaagaagg acaaggaaaa atgttgttcc aagaaacaaa gatgtaagta | 540 |
| aa | 542 |

<210> SEQ ID NO 6
<211> LENGTH: 2125
<212> TYPE: DNA
<213> ORGANISM: Homo sapiens

<400> SEQUENCE: 6

| | |
|---|---|
| gatctatacc taccaccttc ctctacccac cagcatctgc acccaccacc cctccccacc | 60 |
| caccattatc tataccaacc acccctccca acctaccagc atctgcaccc accacaccgc | 120 |
| ccacccacca ccatgtacac tcactacacc ttccagccat caccatctgc acccatcact | 180 |
| cctcccatc cacaagcatc tgcacccacc acatttccct acctaccagc atcttcactc | 240 |
| accacctctc cacccaccag catctgcacc cacaacccct cctcacccac cagagtctgc | 300 |
| atccatcaca cttgcccact cgctagcatc tgcaccatca agctctgcct tcttgcctaa | 360 |
| tacgggatga gctctccatg gttctgccta agacaatgc ttccactcct cttctataac | 420 |
| ccatttcctt ttacctcttc aagtacactt cagaacttct ctctccttct gataccaact | 480 |
| ttttccactt tactcaatca ttcctatcac catacaaacg tgtttatttc tcccatctta | 540 |
| aagttaaaaa tcaaaagaaa attgtctgcg gccaggcacg gtggctcacg cctgtaatcc | 600 |
| caacactttg ggaggccaag gagggttgga tgacttaagg ttaggagttc aagaccagcc | 660 |
| tggccaacat ggtgaaaccc atctctacta aaaatacaaa aattagccag gcatggtggc | 720 |
| acatgcctgt agtctcaggt acttgggagg ctgaggccag agaatggctt gaacccggga | 780 |
| ggcagaggtt gcagtgagcc gagattgtgc ccttgcactc cagcctgggt gacagagtga | 840 |
| gactccatct caaaaataaa aataaaaat aaaacaaaag aaagttattt ttacccaaca | 900 |
| tccacattaa ccaaataccc atttctttat tgatctttgt aaaaaaaagc tcttggaaaa | 960 |
| attgtctata ttcactatga cttatctcct ccaaatcact taaacacata ccaatcaggt | 1020 |
| ttttgttttc atcattccaa agtaacttttt acagccaagg acagtagcga actttacatc | 1080 |
| gcatatgcat tgtgaagttc ttgatcctca tcttacttaa cctgtcagca gtatctgaca | 1140 |
| caggtgtcac tggctcctcc ctgagatgct ctctttattt ggctttgggg acaccatatt | 1200 |
| ctccccattc ctactttcct caatggccct cctcagtctc ctttggaaag aggaaaaaga | 1260 |
| aacttcatta tctcctggat gtagtacaaa caactcaagc tcaacatgtg catactgaac | 1320 |
| tccatttcct tttcccaaac ttcgacattt acagccatcc cctttcagct gatagcaagt | 1380 |
| ttatccttcc agctactcaa accagaatct ttagagccat ccttgaccct tttcctcctc | 1440 |
| tcacactcaa catctatcca tcagaaaatt ttgttggttc tactttcaaa atgcatacag | 1500 |
| agtcagagca tgtctcatta cctccaatag ctaccatact agtctgaaca aacatcattt | 1560 |
| ctcacctggg ttattgaaca aacatcattt ctcacctggg ttattgatag catcctaacg | 1620 |
| ggtcttcctg tttcttggtt ccctatatt agcaacacag cagtcagagg agtccttta | 1680 |
| gaactcaatc agatcatgtc acgtcactcc tctacttaaa atccttcaat gggtcccatt | 1740 |
| acacaaagag tacaaaccag agcccttaca ctggtctaca agttccaaca tttgactcct | 1800 |
| gttatctctc tgcatcata ttctaatatt actgctgttg tcctttttgct ccagtcacac | 1860 |
| tgtttgatta gtaaatattt attaaacaaa gcaatcctag tctccaaaga gatcatagtt | 1920 |

-continued

```
tattggagga aacaagagcc tataaatggt tacacacaga aggtagtgat tatggttctc    1980
cctcacctcc catcctaaac tttgacaggt gaaactcccc tggatgttga aggttgagga    2040
atttgccagg gttcagggtg gtgttggagg aggcagggag gaagcaagga catttcaggc    2100
aggaagaaca ttacatgcaa agatc                                         2125

<210> SEQ ID NO 7
<211> LENGTH: 14
<212> TYPE: DNA
<213> ORGANISM: Homo sapiens
<220> FEATURE:
<221> NAME/KEY: misc_feature
<222> LOCATION: (1)...(14)
<223> OTHER INFORMATION: n = A,T,C or G

<400> SEQUENCE: 7
yyyyyyyyyy nyag                                                     14
```

GENOMIC SEQUENCES FOR PROTEIN PRODUCTION AND DELIVERY

CROSS REFERENCE TO RELATED APPLICATIONS

This application claims the benefit of U.S. Provisional Application Ser. No. 60/084,663, filed May 7, 1998, herein incorporated by reference.

FIELD OF THE INVENTION

This invention relates to genomic DNA.

BACKGROUND OF THE INVENTION

Current approaches to treating disease with therapeutic proteins include both administration of proteins produced in vitro and gene therapy. In vitro production of a protein generally involves the introduction of exogenous DNA coding for the protein of interest into appropriate host cells in culture. Gene therapy methods, on the other hand, involve administering to a patient genetically engineered cells, plasmids, or viruses that contain a sequence encoding the therapeutic protein of interest.

Certain therapeutic proteins may also be produced by altering the expression of their endogenous genes in a desired manner with gene targeting techniques. See, e.g., U.S. Pat. Nos. 5,641,670, 5,733,761, and 5,272,071; WO 91/06666; WO 91/06667; and WO 90/11354, all of which are incorporated by reference in their entirety.

SUMMARY OF THE INVENTION

The present invention is based upon the identification and sequencing of genomic DNA 5' to the coding sequences of the human follicle-stimulating hormone β ("FSHβ") gene. This DNA can be used, for example, in a DNA construct that alters (e.g., increases) expression of an endogenous FSHβ gene in a mammalian cell upon integration into the genome of the cell via homologous recombination. "Endogenous FSHβ gene" refers to a genomic (i.e., chromosomal) copy of a gene that encodes FSHβ. The construct contains a targeting sequence including or derived from the newly disclosed 5' noncoding sequence, and a transcriptional regulatory sequence. The transcriptional regulatory sequence preferably differs in sequence from the transcriptional regulatory sequence of the endogenous FSHβ gene. The targeting sequence directs the integration of the regulatory sequence into a region witthin or upstream of the FSHβ-coding sequences of the target gene such that the regulatory sequence becomes operatively linked to the endogenous coding sequence. By "operatively linked" is meant that the regulatory sequence can direct expression of the endogenous FSHβ-coding sequence. The construct may additionally contain a selectable marker gene to facilitate selection of cells that have stably integrated the construct, and/or another coding sequence operatively linked to a promoter.

In one embodiment, the DNA construct contains: (a) a targeting sequence, (b) a regulatory sequence, (c) an exon, and (d) a splice-donor site. The targeting sequence directs the integration of itself and elements (b)–(d) into a region within or upstream of the FSHβ-coding sequences of the target gene. Once integrated, element (b) can direct transcription of elements (c) and (d) and all downstream coding sequences of the endogenous gene. In the construct, the exon is generally 3' of the regulatory sequence, and the splice-donor site is at the 3' end of the exon.

In another embodiment, the DNA construct comprises: (a) a targeting sequence, (b) a regulatory sequence, (c) an exon, (d) a splice-donor site, (e) an intron, and (f) a splice-acceptor site, wherein the targeting sequence directs the integration of itself and elements (b)–(f) such that elements (b)–(f) are within or upstream of the endogenous gene. The regulatory sequence then directs production of a transcript that includes not only elements (c)–(f), but also the endogenous FSHβ coding sequence. Preferably, the intron and the splice-acceptor site are situated in the construct downstream from the splice-donor site.

The targeting sequence is homologous to a pre-selected target site in the genome with which homologous recombination is to occur. It contains at least 20 (e.g., at least 30, 50, 100, or 1000) contiguous nucleotides from SEQ ID NO:4, which corresponds to nucleotides −7454 to −1417 of human FSHβ genomic sequence (numbering relative to the translation start site), or SEQ ID NO:5, which corresponds to nucleotides −696 to −155 of human FSHβ genomic sequence. By "homologous" is meant that the targeting sequence is identical or sufficiently similar to its genomic target site so that the targeting sequence and target site can undergo homologous recombination within a human cell. A small percentage of basepair mismatches is acceptable, as long as homologous recombination can occur at a useful frequency. To facilitate homologous recombination, the targeting sequence is preferably at least about 20 (e.g., at least 50, 100, 250, 400, or 1,000) base pairs ("bp") long. The targeting sequence can also include genomic sequences from outside the region covered by SEQ ID NO:4 or 5, so long as it includes at least 20 nucleotides from within one of the two regions. For example, additional targeting sequence could be derived from the sequence lying between SEQ ID NO:4 and the transcription initiation sequence of the FSHβ gene.

Due to polymorphism that may exist at the FSHβ genetic locus, minor variations in the nucleotide composition of any given genomic target site may occur in any given mammalian species. Targeting sequences that correspond to such polymorphic variants (particularly human polymorphic variants) of SEQ ID NO:4 or 5 are within the scope of this invention.

Upon homologous recombination, the regulatory sequence of the construct is integrated into a pre-selected region upstream of the coding sequence of a FSHβ gene in a chromosome of a cell. The resulting new transcription unit containing the construct-derived regulatory sequence alters the expression of the target FSHβ gene. The FSHβ protein so produced may be identical in sequence to the FSHβ protein encoded by the unaltered, endogenous gene, or may contain additional, substituted, or fewer amino acid residues as compared to the wild type FSHβ protein, due to changes introduced as a result of homologous recombination.

Altering gene expression encompasses activating (or causing to be expressed) a gene which is normally silent (i.e., essentially unexpressed) in the cell as obtained, increasing or decreasing the expression level of a gene, and changing the regulation pattern of a gene such that the pattern is different from that in the cell as obtained. "Cell as obtained" refers to the cell prior to homologous recombination.

Also within the scope of the invention is a method of using the present DNA construct to alter expression of an endogenous FSHβ gene in a mammalian cell. This method includes the steps of (i) introducing the DNA construct into the mammalian cell, (ii) maintaining the cell under conditions that permit homologous recombination to occur between the construct and a genomic target site homologous to the targeting sequence, to produce a homologously recombinant cell; and (iii) maintaining the homologously recombinant cell under conditions that permit expression of the FSHβ-coding sequence under the control of the construct-derived regulatory sequence. At least a part of the genomic target site is 5' to the coding sequence of an endogenous FSHβ gene. That is, the genomic target site can contain coding sequence as well as 5' non-coding sequence.

The invention also features transfected or infected cells in which the construct has undergone homologous recombination with genomic DNA upstream of the endogenous ATG initiation codon in one or both alleles of the endogenous FSHβ gene. Such transfected or infected cells, also called homologously recombinant cells, have an altered FSHβ expression pattern. These cells are particularly useful for in vitro FSHβ production and for delivering FSHβ via gene therapy. Methods of making and using such cells are also embraced by the invention. The cells can be of vertebrate origin such as mammalian (e.g., human, non-human primate, cow, pig, horse, goat, sheep, cat, dog, rabbit, mouse, guinea pig, hamster, or rat) origin.

The invention further relates to a method of producing a mammalian FSHβ protein in vitro or in vivo by introducing the above-described construct into the genome of a host cell via homologous recombination. The homologously recombinant cell is then maintained under conditions that allow transcription, translation, and optionally, secretion of the FSHβ protein.

The invention also features isolated nucleic acids comprising a sequence of at least 20 (e.g., at least 30, 50, 100, 200, or 1000) contiguous nucleotides of SEQ ID NO:4, or at least 20 (e.g., at least 30, 50, 100, or 200) contiguous nucleotides of SEQ ID NO:5, or of a similar-sized portion of a sequence identical to SEQ ID NO:4 or 5 except for polymorphic variations or other minor variations (e.g., less than 5% of the sequence) which do not prevent homologous recombination with the target sequence.

In one embodiment, the isolated nucleic acid of the invention includes a contiguous 100 bp block of SEQ ID NO:4 or 5. For example, the isolated DNA can contain nucleotides 1 to 100, 101 to 200, 201 to 300, 301 to 400, 401 to 500, 501 to 600, 601 to 700, 701 to 800, 801 to 900, 901 to 1000, 1001 to 1100, 1101 to 1200, 1201 to 1300, 1301 to 1400, 1401 to 1500, 1501 to 1600, 1601 to 1700, 1701 to 1800, 1801 to 1900, 1901 to 2000, 2001 to 2100, 2101 to 2200, 2201 to 2300, 2301 to 2400, 2401 to 2500, 2501 to 2600, 2601 to 2700, 2701 to 2800, 2801 to 2900, 2901 to 3000, 3001 to 3100, 3101 to 3200, 3201 to 3300, 3301 to 3400, 3401 to 3500, 3501 to 3600, 3601 to 3700, 3701 to 3800 3801 to 3900, 3901 to 4000, 4001 to 4100, 4101 to 4200, 4201 to 4300, 4301 to 4400, 4401 to 4500, 4501 to 4600, 4601 to 4700, 4701 to 4800, 4801 to 4900, 4901 to 5000, 5001 to 5100, 5101 to 5200, 5201 to 5300, 5301 to 5400, 5401 to 5500, 5501 to 5600, 5601 to 5700, 5701 to 5800, 5801 to 5900, 5901 to 6000, or 5939 to 6038 of SEQ ID NO:4 or its complement. Alternatively, the isolated nucleic acid of the invention can include nucleotides 1 to 100, 101 to 200, 201 to 300, 301 to 400, 401 to 500, or 443 to 542 of SEQ ID NO:5. These blocks of SEQ ID NO:4 or 5 or their complements are useful as targeting sequences in the constructs of the invention.

In the isolated DNA, the contiguous nucleotide sequence is not linked to a sequence encoding full-length FSHβ, or at least not linked in the same configuration (i.e., separated by the same sequence) as in any native genome. The term "isolated DNA", as used herein, thus does not denote a chromosome or large piece of genomic DNA (as might be incorporated into a cosmid or yeast artificial chromosome) that includes not only part or all of SEQ ID NO:4 or 5, but also an intact FSHβ-coding sequence and all of the sequence which lies between the FSHβ coding sequence and the sequence corresponding to SEQ ID NO:4 or 5 as it exists in the genome of a cell. It does include, but is not limited to, a DNA (i) which is incorporated into a plasmid or virus; or (ii) which exists as a separate molecule independent of other sequences, e.g., a fragment produced by polymerase chain reaction ("PCR") or restriction endonuclease treatment. The isolated DNA preferably does not contain a sequence which encodes intact FSHβ precursor (i.e., FSHβ complete with its endogenous secretion signal peptide).

The invention also includes isolated DNA comprising a strand which contains a sequence that is at least 100 (e.g., at least 200, 400, or 1000) nucleotides in length and that hybridizes under either highly stringent or moderately stringent conditions with SEQ ID NO:4 or 5, or the complement of SEQ ID NO:4 or 5. The sequence is not linked to a PSHβ-coding sequence, or at least not linked in the same configuration as occurs in any native genome. By moderately stringent conditions is meant hybridization at 50° C. in Church buffer (7% SDS, 0.5% NaHPO$_4$, 1 M EDTA, 1% bovine serum albumin) and washing at 50° C. in 2×SSC. Highly stringent conditions are defined as hybridization at 42° C. in the presence of 50% formamide; a first wash at 65° C. with 2×SSC containing 1% SDS; followed by a second wash at 65° C. with 0.1×SSC.

Also embraced by the invention is isolated DNA comprising a strand which contains a sequence that (i) is at least 100 (e.g., at least 200, 400, or 1000) nucleotides in length and (ii) shares at least 80% sequence (e.g., 85%, 90%, 95%, or 98%) identity with a segment of equal length from SEQ ID NO:4 or 5, or from the complement of SEQ ID NO:4 or 5. The sequence is not linked to a FSHβ-coding sequence, or at least not linked in the same configuration as occurs in any native genome.

Where a particular polypeptide or nucleic acid molecule is said to have a specific percent identity or conservation to a reference polypeptide or nucleic acid molecule, the percent identity or conservation is determined by the algorithm of Myers and Miller, CABIOS (1989), which is embodied in the ALIGN program (version 2.0), or its equivalent, using a gap length penalty of 12 and a gap penalty of 4 where such parameters are required. All other parameters are set to their default positions. Access to ALIGN is readily available. See, e.g., http://www2.igh.cnrs.fr/bin/align-guess.cgi on the Internet.

The invention also features a method of delivering FSHβ to an animal (e.g., a mammal such as a human, non-human primate, cow, pig, horse, goat, sheep, cat, dog, rabbit, mouse, guinea pig, hamster, or rat) by providing a cell whose endogenous FSHβ gene has been activated as described herein, and implanting the cell in the animal, where the cell secretes FSHβ. Also included in the invention is a method of producing FSHβ by providing a cell whose endogenous FSHβ gene has been activated as described herein, and culturing the cell in vitro under conditions which permit the cell to express and secrete FSHβ.

The isolated DNA of the invention can be used, for example, as a source of an upstream PCR primer for use (when combined with a suitable downstream primer) in obtaining the regulatory and/or coding regions of an endogenous FSHβ gene, or as a hybridization probe for indicating the presence of chromosome 11 in a preparation of human chromosomes. It can also be used, as described below, in a method for altering the expression of an endogenous FSHβ gene in a vertebrate cell.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications, patent applications, patents, and other references mentioned herein are incorporated by reference in their entirety. In case of conflict, the present specification, including definitions, will control. The materials, methods, and examples are illustrative only and not intended to be limiting.

Other features and advantages of the invention will be apparent from the following detailed description, and from the claims.

BRIEF DESCRIPTION OF THE DRAWINGS

FIG. 3 a representation of a partial sequence (SEQ ID NO:1) of a human FSHβ gene, including 7,454 nucleotides of the sequence 5' to the ATG initiation codon. Also shown is a partial polypeptide sequence (SEQ ID NO:2) encoded by the coding sequence. Published sequences are underlined. "SD" and "SA" stand for splice-donor site and splice-acceptor site, respectively. "Mature" denotes the beginning of a mature FSHβ protein.

FIG. 9 is a representation of SEQ ID NO:4, a sequence upstream of a human FSHβ transcription start site.

FIG. 10 is a representation of SEQ ID NO:5, a sequence upstream of a human FSHβ transcription start site.

FIG. 11 is a representation of a first targeting sequence (SEQ ID NO: 6) used in a construct of the invention.

FIG. 12 is a representation of a second targeting sequence (SEQ ID NO: 5) used in a construct of the invention.

DETAILED DESCRIPTION

The present invention is based on the discovery of the nucleotide composition of sequences upstream to the coding sequence of a human FSHβ gene.

FSH is a gonadotrophin which plays an essential role in the maintenance and development of oocytes and spermatozoa in normal reproductive physiology. FSH possesses two subunits, α and β, the latter being responsible for FSH's biological specificity.

Figure 1:
FIG. 1 is a schematic diagram showing the genomic structure of the human FSHβ gene.

The human FSHβ gene encodes a 129 amino acid precursor protein containing a 16 amino acid signal peptide. The gene contains three exons and two introns, with the first exon being a non-coding exon. The genomic map of the human FSHβ gene is shown in FIG. 1. The map is constructed based on published sequences (HUMFSHBQ1, GenBank accession numbers M54912, M38644, M21219, and M18536) that correspond to three separate genomic segments (FIG. 1). The first segment is 720 bp long and contains 530 bp of nontranscribed upstream sequences, exon 1 (63 bp; non-coding), and 127 bp of intron 1. The second segment begins at position −152 and ends at position +367 (all positions referred to herein are relative to the translational initiation site, unless specified otherwise). This segment includes 146 bp of intron 1, exon 2 (165 bp), and 208 bp of intron 2. The third segment contains 102 bp of intron 2 and exon 3, and extends 1,480 bp past the translational stop codon.

Specific Sequences 5' to a FSHβ Coding Sequence and Their Use in Altering Endogenous FSHβ Gene Expression To obtain genomic DNA containing sequence upstream to a FSHβ gene, a human leukocyte genomic library in lambda EMBL3 (Clontech catalog # HL1006d) was screened with a 40 bp oligonucleotide probe, BETA2. This probe is derived from 23 bp of exon 1 and 17 bp of intron 1, and has the following sequence:

5'TTGGCATCTACCGTTTTCAAGTGGTGACAGCTACTTTTGA 3' (SEQ ID NO:3)

Figure 2:
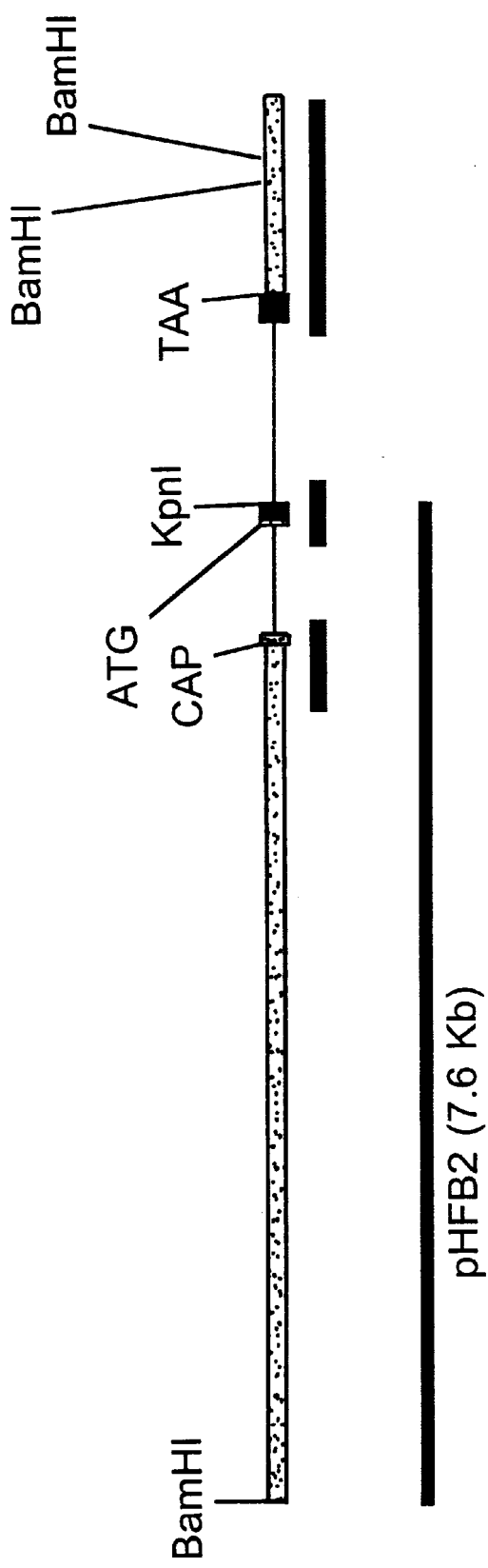
FIG. 2 is a schematic diagram showing the genomic region of the human FSHβ gene (top) encompassed by the insert (bottom) of plasmid pHFB2. The three bars in the middle represent genomic regions of the gene whose sequences have been published.

Approximately one million recombinant phage were screened with the radiolabelled BETA2 probe. One phage plaque, designated clone 8-1-1-1, was isolated. The 7.6 kb HindIII-KpnI fragment from phage 8-1-1-1 was subcloned into pBluescript II SK+ (Stratagene, La Jolla, Calif.) to produce a plasmid containing about 6.6 kb of upstream sequences, exon 1, intron 1, exon 2, and 9 bp of intron 2 (FIG. 2). The plasmid was designated pHFB2.

The pHFB2 plasmid was sequenced by the Sanger method. The sequence data sets were aligned to obtain the complete sequence of the entire phage 8-1-1-1 insert. This nucleotide sequence (SEQ ID NO:1) is shown in FIG. 3.

The insert was shown to encompass a 7,622 bp region of the FSHβ gene, starting at position −7,454 (FIG. 3). The sequences encompassing positions −7,454 to −1,417 (6,038 bp of the upstream sequence; SEQ ID NO:4) and positions −696 to −155 (542 bp of intron 1; SEQ ID NO:5) have not been reported previously.

Figure 4:
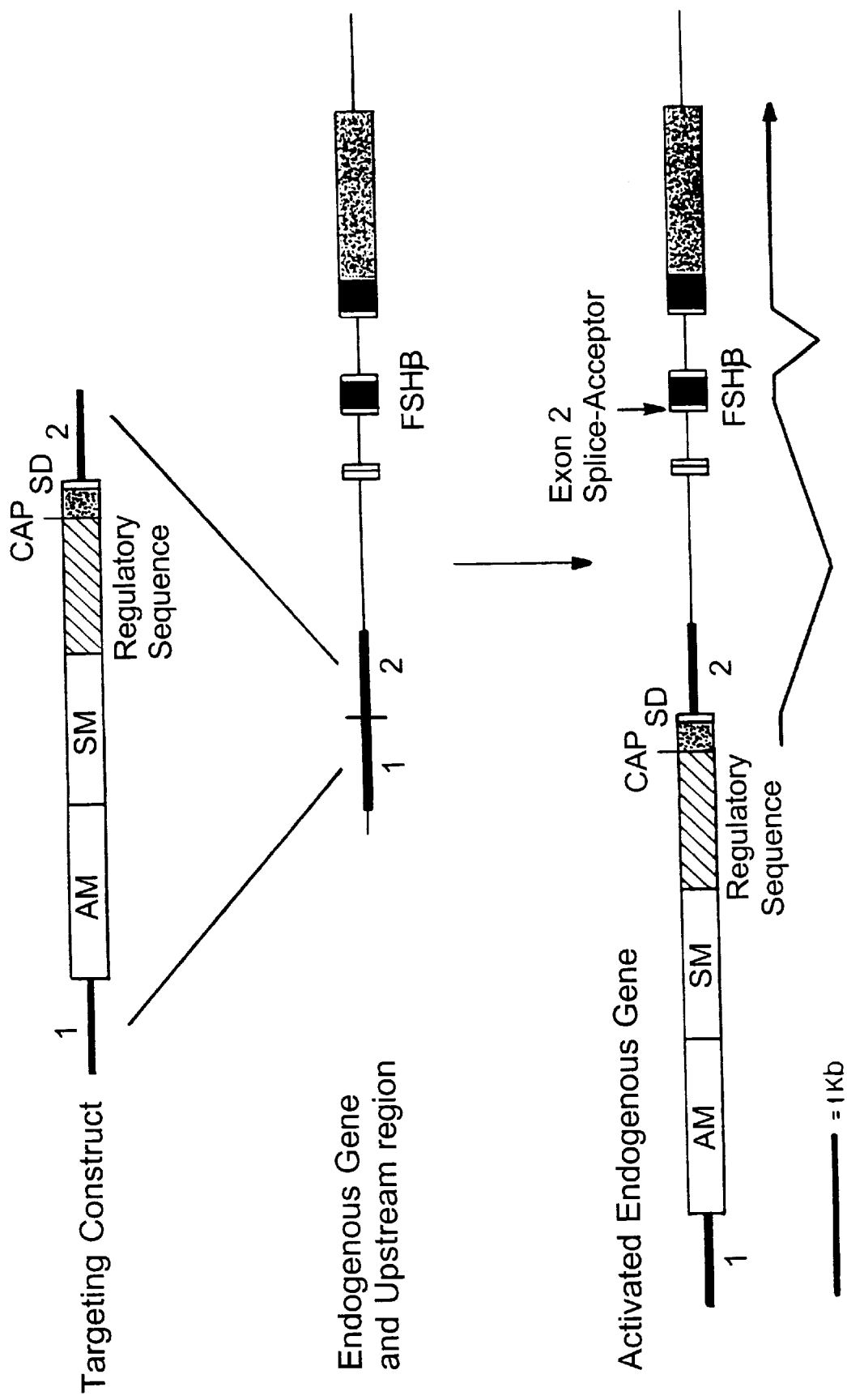
FIG. 4 is a schematic diagram showing a construct of the invention. The construct contains a first targeting sequence (1); an amplifiable marker gene (AM); a selectable marker gene (SM); a regulatory sequence; a CAP site; a sequence identical to the first, non-coding exon of a human FSHβ gene; an unpaired splice-donor site (SD); and a second targeting sequence (2). The black boxes represent coding DNA and the stippled boxes represent untranslated sequences.
Figure 5:
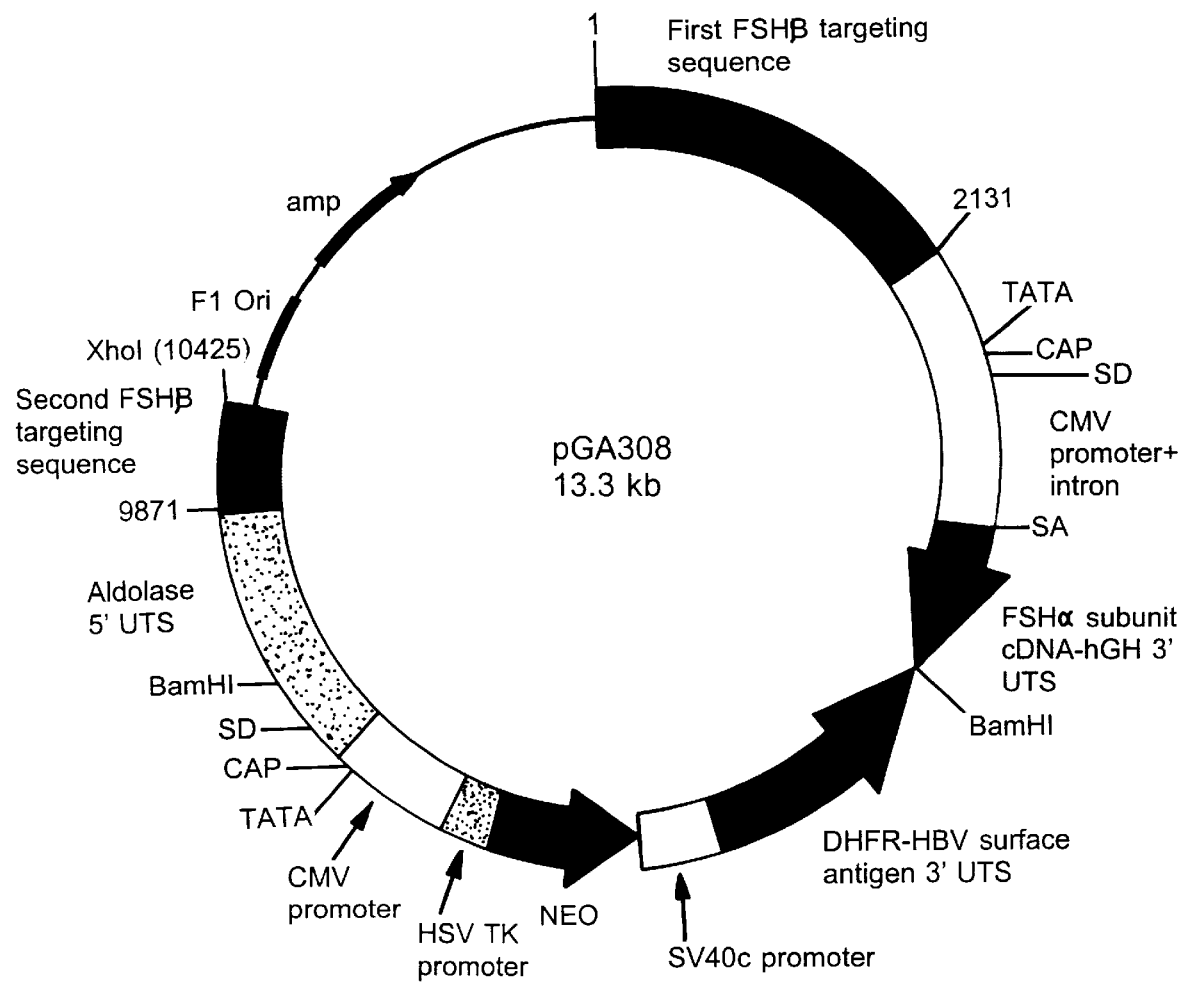
FIGS. 5–7 are schematic diagrams illustrating three constructs of the invention. The constructs differ in the size of the aldolase 5' UTS inserted into the plasmid. These constructs include a sequence encoding a glycoprotein α-subunit (i.e, FSHα) linked to a cytomegalovirus ("CMV") promoter. The abbreviations shown in the figure are: "UTS" for untranslated sequence; "amp" for ampicillin; "Ori" for replication origin,; "SD" for splice-donor site; "HSV TK" for herpes simplex virus thymidine kinase gene; "DHFR" for dihydrofolate reductase; "HBV" for hepatitis B virus; and "hGH" for human growth hormone.
Figure 6:
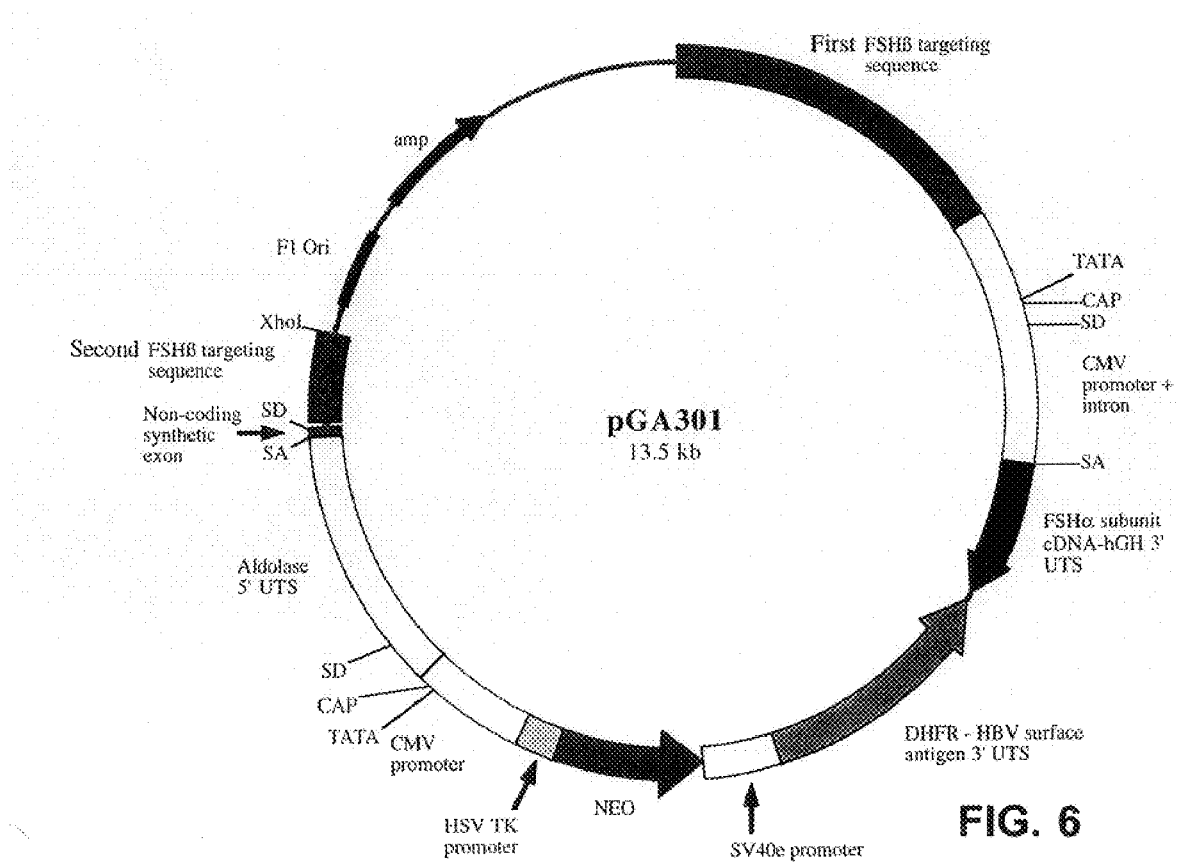
Figure 7:
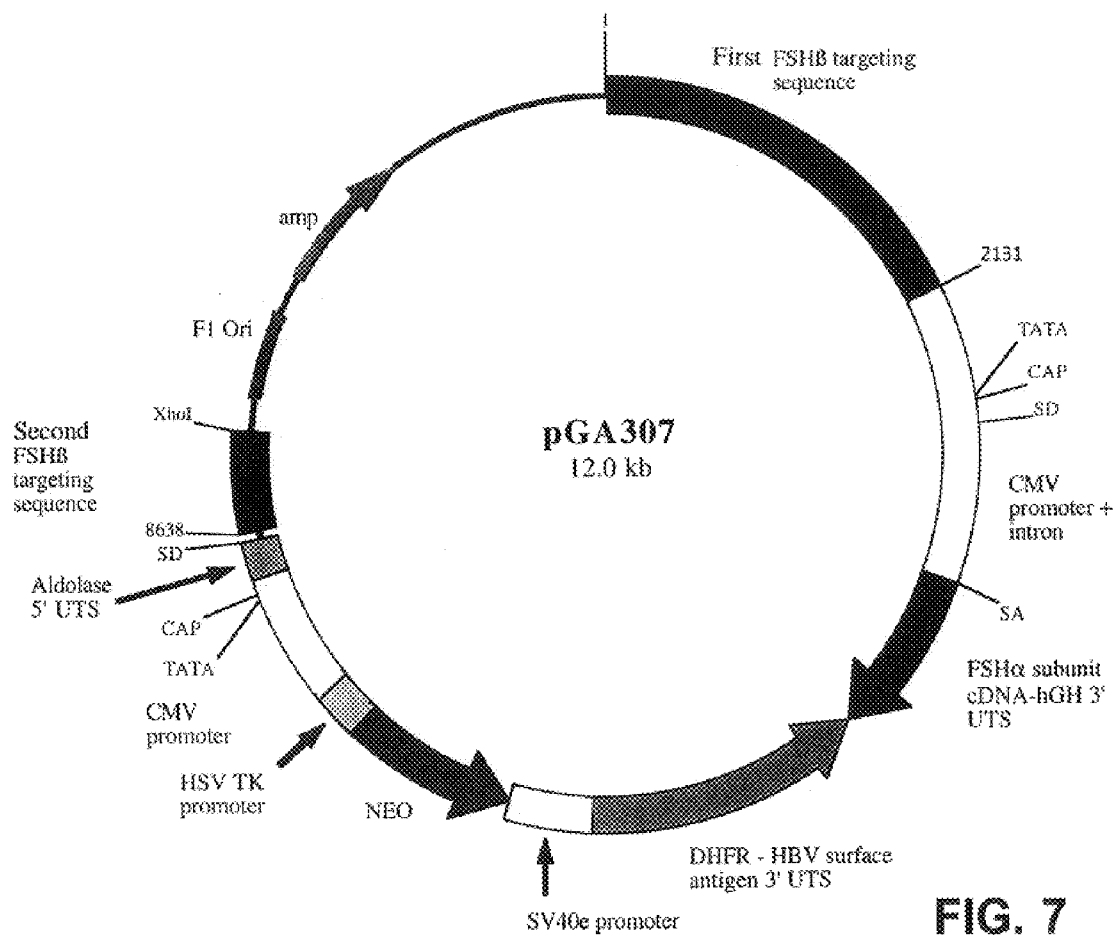

To alter the expression of an endogenous FSHβ gene, the general approach shown in FIG. 4 was used. Nucleotides 3860 to 5784 of SEQ ID NO:4 served as the first (5') targeting sequence, while SEQ ID NO:5 served as the second (3') targeting sequence. DNA fragments containing these sequences were then subcloned into plasmids to produce targeting constructs pGA308, pGA301, and pGA307, which are illustrated in FIGS. 5–7, respectively. These plasmids each contain about a 3.2 Kb 5' targeting sequence and about a 0.5 Kb 3' targeting sequence.

HT-1080 cells were separately transfected with each of the plasmids and placed under G418 selection. After approximately 14 days, G418 resistant colonies in 6-well plates were counted. In addition, the conditioned medium in each well was screened for GA-FSH expression by ELISA. Cells exhibiting GA-FSH production were trypsinized and counted. The cells were then diluted and plated in 96-well plates to generate clones. After about two weeks of culture, clonal cell populations were screened for GA-FSH production by ELISA. Colonies found to produce GA-FSH were expanded in culture and stored or further analyzed. Table 1 summarizes the endogenous gene activation frequency and other observations from the above cloning procedure.

Figure 8:
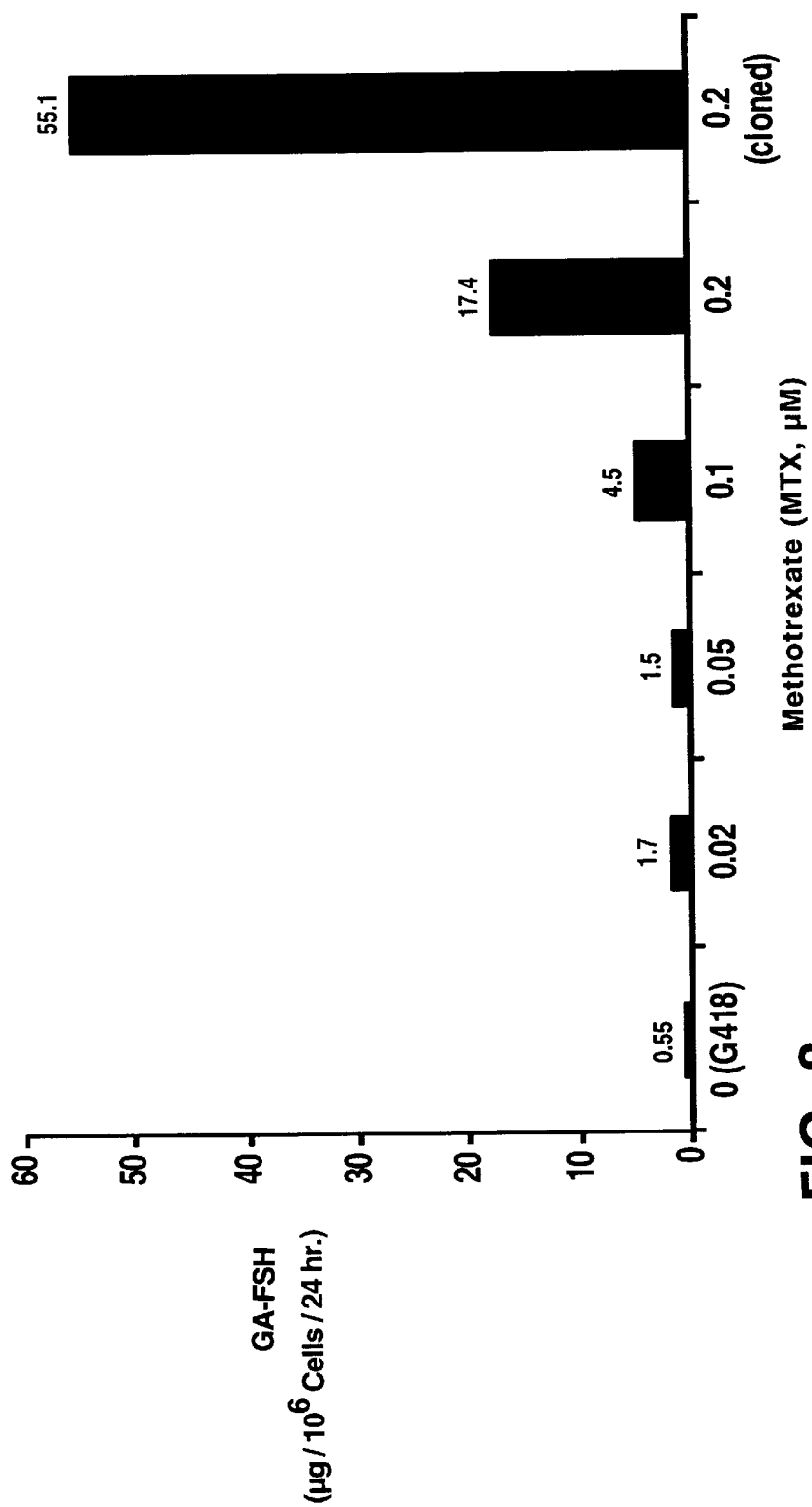
FIG. 8 is a bar graph of FSH production from HT-1080 cells transfected with pGA308 (FIG. 5) and selected for growth in the presence of various concentrations of methotrexate.

The cells transfected with pGA308 were studied in more detail. FIG. 8 indicates the range of FSH production achieved in pGA308-transfected HT1080 cells cultured in media having various concentrations of methotrexate. The bar labeled "0.2 (cloned)" represents the FSH production from a cell line cloned by limiting dilution of cells resistant to 0.2 $\mu$M methotrexate. The results graphed in FIG. 8 clearly indicate that higher concentrations of methotrexate can yield cell lines that produce at least 50 $\mu$g/$10^6$ cells in a day.

sequence. For this strategy, the 5' end of the second target site is preferably less than 40 bp upstream of the normal FSH$\beta$ transcriptional start site, in order to avoid undesired ATG start codons. A mRNA precursor produced from the homologously recombined locus will include the exogenous exon, the exogenous splice-donor site, the exogenous intron, the exogenous splice-acceptor site, and any sequences between the exogenous splice acceptor site and the transcription termination site of the endogenous FSH$\beta$ gene. Splicing of this transcript will generate a mRNA which can be translated to produce a precursor of human FSH$\beta$, having either the normal FSH$\beta$ secretion signal sequence or a genetically engineered secretion signal sequence. The size of the exogenous intron and thus the position of the exogenous regulatory region relative to the coding region of the endogenous gene can be varied to optimize the function of the regulatory region.

In any activation strategy, the first and second target sites need not be immediately adjacent or even be near each other. When they are not immediately adjacent to each other, a portion of the FSH$\beta$ gene's normal upstream region and/or a portion of the coding region would be deleted upon homologous recombination.

TABLE 1

| Plasmid Transfected | Total No. G418-Resistant Colonies | Total No. FSH$\beta$ Gene Activation Events | Activation Frequency | Total No. Clonal Cell Lines Isolated | Average FSH$\beta$ Production (ng/$10^6$ cells in 24 hours) |
|---|---|---|---|---|---|
| pGA301 | 38012 | 3 | 1/12671 | 11 | 465 |
| pGA307 | 31068 | 3 | 1/10356 | 20 | 450 |
| pGA308 | 27474 | 4 | 1/6869 | 16 | 521 |

General Methodologies
Alteration of Endogenous FSH$\beta$ Expression

Using the above-described FSH$\beta$ upstream sequences, one can alter the expression of an endogenous human FSH$\beta$ gene by a method as generally described in U.S. Pat. No. 5,641,670. One strategy is shown in FIG. 4. In this strategy, a targeting construct is designed to include a first targeting sequence homologous to a first target site upstream of the gene, an amplifiable marker gene, a selectable marker gene, a regulatory region, a CAP site, an exon, an unpaired splice-donor site, and a second targeting sequence corresponding to a second target site downstream of the first target site, and terminating either within or upstream of the FSH$\beta$-coding sequence. In this strategy, the first and second target sites are immediately adjacent in the chromosome prior to homologous recombination, but such configuration is not required (see also below). Homologously recombinant cells will produce an mRNA precursor which corresponds to the exogenous exon and splice-donor site, and any sequence between the splice donor site and the transcription termination sequence of the FSH$\beta$ gene, including the FSH$\beta$ introns, exons, and 3' untranslated region (FIG. 4). Splicing of this message results in a mRNA in which the exogenous exon is fused to exon 2 of the endogenous FSH$\beta$ gene. Translation of the mRNA produces a precursor FSH$\beta$.

Other approaches can also be employed. For example, the first and/or second target sites can be in the first intron of the FSH$\beta$ gene. Alternatively, the DNA construct may be designed to include, from 5' to 3', a first targeting sequence, an amplifiable marker gene, a selectable marker gene, a regulatory region, a CAP site, an exon, a splice-donor site, an intron, a splice-acceptor site, and a second targeting If desired, the product of the activated FSH$\beta$ gene can be produced in a cell type that expresses a human glycoprotein $\alpha$-subunit (FSH$\alpha$) gene, the product of which forms a heterodimer with the product of the FSH$\beta$ gene. This may be a naturally occurring cell strain or cell line. Alternatively, the human glycoprotein $\alpha$-subunit gene (Genbank sequence HUMGLYCA1) can be co-expressed with the product of the FSH$\beta$ gene, with such co-expression accomplished by expression of the human glycoprotein $\alpha$-subunit gene or cDNA under the control of a suitable promoter, or by activation of the human glycoprotein $\alpha$-subunit gene through the methods described herein.

By way of example, a sequence coding for a glycoprotein $\alpha$-subunit can be included in the DNA construct. This coding sequence is placed under the transcriptional control of a regulatory sequence that has a nucleotide composition that may be identical to or different from that of the regulatory sequence that is to direct expression of the endogenous FSH$\beta$ gene. FIGS. 5–7 illustrate examples of such constructs.

The DNA Construct

The DNA construct of the invention includes at least a targeting sequence and a regulatory sequence. It may additionally contain an exon; or an exon and an unpaired splice-donor site; or an exon, splice donor site, intron, and splice acceptor site. The exon, if present, is 3' of the regulatory sequence, and the unpaired splice-donor site is at the 3' end of the exon. The intron and splice acceptor site, if present, are 3' of the splice donor site. In addition, there can be multiple exons and introns (with appropriate splice donor and acceptor sites) preceding (i.e., 5' to) the exon flanked by the unpaired splice-donor site. The DNA in the construct is referred to as exogenous, since the DNA is not an original part of the genome of a host cell. Exogenous DNA may possess sequences identical to or different from portions of the endogenous genomic DNA present in the cell prior to transfection or infection by viral vector. As used herein, "transfection" means introduction of plasmid into a cell by chemical and physical means such as calcium phosphate or calcium chloride co-precipitation, DEAE-dextran-mediated transfection, lipofection, electroporation, microinjection, microprojectiles, or biolistic-mediated uptake. As used herein "infection" means introduction of viral nucleic acid into a cell by virus infection. The various elements included in the DNA construct of the invention are described in detail below.

The DNA construct can also include cis-acting or trans-acting viral sequences (e.g., packaging signals), thereby enabling delivery of the construct into the nucleus of a cell via infection by a viral vector. Where necessary, the DNA construct can be disengaged from various steps of a virus life cycle, such as integrase-mediated integration in retroviruses or episome maintenance. Disengagement can be accomplished by appropriate deletions or mutations of viral sequences, such as a deletion of the integrase coding region in a retrovirus vector. Additional details regarding the construction and use of viral vectors are found in Robbins et al., Pharmacol. Ther. 80:35–47, 1998; and Gunzburg et al., Mol. Med. Today 1:410–417, 1995, herein incorporated by reference.

Targeting Seauences

Targeting sequences permit homologous recombination of a desired sequence into a selected site in the host genome. Targeting sequences are homologous to (i.e., able to homologously recombine with) their respective target sites in the host genome.

A circular DNA construct can employ a single targeting sequence, or two or more separate targeting sequences. A linear DNA construct may contain two or more separate targeting sequences. The target site to which a given targeting sequence is homologous can reside within an exon and/or intron of the FSHβ gene, upstream of and immediately adjacent to the FSHβ-coding region, or upstream of and at a distance from the FSHβ-coding region.

The first of the two targeting sequences in the construct (or the entire targeting sequence, if there is only one targeting sequence in the construct) is at least in part derived from the newly disclosed genomic regions upstream of the FSHβ-coding sequences. This targeting sequence contains a portion of SEQ ID NO:1, e.g., at least 20 consecutive nucleotides from the sequence corresponding to positions −7,454 to −1,417 (SEQ ID NO:4) or to positions −696 to −155 (SEQ ID NO:5). The second of the two targeting sequences in the construct may target a genomic region upstream of the coding sequence (e.g., also contain a portion of SEQ ID NO:4 or 5), or target an exon or intron of the gene.

The targeting sequence(s) may additionally include sequence derived from a previously known region of the FSHβ gene, including those described herein, as well as regions further upstream which are structurally uncharacterized but can be mapped by one skilled in the art.

Genomic fragments that can be used as targeting sequences can be identified by their ability to hybridize to a probe containing all or a portion of SEQ ID NO:4 or 5. Such a probe can be generated by PCR using primers derived from SEQ ID NO:1.

The Regulatory Seauence

The regulatory sequence of the DNA construct can contain one or more promoters (e.g., a constitutive, tissue-specific, or inducible promoter), enhancers, scaffold-attachment regions or matrix attachment sites, negative regulatory elements, transcription factor binding sites, or combinations of these elements.

The regulatory sequence can be derived from a eukaryotic (e.g., mammalian) or viral genome. Useful regulatory sequences include, but are not limited to, those that regulate the expression of SV40 early or late genes, cytomegalovirus genes, and adenovirus major late genes. They also include regulatory regions derived from genes encoding mouse metallothionein-I, elongation factor-1α, collagen (e.g., collagen Iα1, collagen Iα2, and collagen IV), actin (e.g., γ-actin), immunoglobulin, HMG-CoA reductase, glyceraldehyde phosphate dehydrogenase, 3-phosphoglyceratekinase, collagenase, stromelysin, fibronectin, vimentin, plasminogen activator inhibitor I, thymosin β4, tissue inhibitors of metalloproteinase, ribosomal proteins, major histocompatibility complex molecules, and human leukocyte antigens.

The regulatory sequence preferably contains transcription factor binding site, such as a TATA Box, CCAAT Box, AP1, Sp1, or a NF-κB binding site.

Marker Genes

If desired, the construct can include a sequence encoding a desired polypeptide, operatively linked to its own promoter. An example of this would be a selectable marker gene, which can be used to facilitate the identification of a targeting event. An amplifiable marker gene can also be used to facilitate selection of cells having co-amplified flanking DNA sequences. Cells containing amplified copies of the amplifiable marker gene can be identified by growth in the presence of an agent that selects for the expression of the amplifiable gene. The activated endogenous gene will typically be amplified in tandem with the amplified selectable marker gene. Cells containing multiple copies of the activated endogenous gene may produce very high levels of FSHβ and are thus useful for in vitro protein production and gene therapy.

The selectable and amplifiable marker genes do not have to lie immediately adjacent to each other. The amplifiable marker gene and selectable marker gene can be the same gene. One or both of the marker genes can be situated in the intron of the DNA construct. Suitable amplifiable marker genes and selectable marker genes are described in U.S. Pat. No. 5,641,670.

The Exogenous Exon

The DNA construct may further contain an exon, i.e., a DNA sequence that is copied into RNA and is present in a mature mRNA molecule. The exon in the construct is referred to herein as an exogenous or construct-derived exon. The exogenous exon can be non-coding, like the first exon of the human FSHβ gene, and in fact can optionally be identical in sequence to the latter exon. Alternatively, the exogenous exon encodes one or more amino acid residues, or partially encodes an amino acid residue (i.e., contains one or two nucleotides of a codon). When the exon contains a coding sequence, the DNA construct should be designed such that, upon transcription and splicing, the reading frame of the resulting mRNA is in-frame with the coding region of the target FSHβ gene. That is, the exogenous exon is spliced to an endogenous exon in a manner that does not change the appropriate reading frame of the portion of the mRNA derived from the endogenous exon.

The inclusion of a coding exon in the DNA construct allows the production of a fusion protein that contains both endogenous FSHβ protein sequence and exogenous protein sequence. Such a hybrid protein may combine the structural, enzymatic, or ligand- or receptor-binding properties from two or more proteins into one polypeptide. For example, the exogenous exon can encode a cell membrane anchor, a signal peptide to improve cellular secretion, a leader sequence, an enzymatic region, a co-factor binding region, or an epitope tag to facilitate purification of the FSHβ hybrid protein produced from the recombined gene locus.

The Splice-Donor Site

The exogenous exon is flanked at its 3' end by a splice-donor site. A splice-donor site is a sequence which directs the splicing of one exon of an RNA transcript to the splice-acceptor site of another exon of the RNA transcript. Typically, the first exon lies 5' of the second exon, and the splice-donor site located at the 3' end of the first exon is paired with a splice-acceptor site on the 5' side of the second exon. Splice-donor sites have a characteristic consensus sequence represented as (A/C)AGGURAGU (where R denotes a purine), with the GU in the fourth and fifth positions being required (Jackson, Nucleic Acids Research 19:3715–3798, 1991). The first three bases of the splice-donor consensus site are the last three bases of the exon: i.e., they are not spliced out. Splice-donor sites are functionally defined by their ability to effect the appropriate reaction within the mRNA splicing pathway.

By way of example, the splice-donor site can be placed immediately adjacent and 3' to an ATG codon when the presence of one or more intervening nucleotides is not required for the exogenous exon to be in-frame with the second exon of the targeted gene. When the exogenous exon encodes one or more amino acids in-frame with the coding sequence of the targeted gene, the splice-donor site may preferably be placed immediately adjacent to the exogenous coding sequence on its 3' side.

The splice-donor site flanking the exogenous exon is unpaired in the construct, i.e., in the construct itself there is no accompanying splice-acceptor site downstream of the splice-donor site to which the latter can be spliced. Following homologous recombination into the target site upstream of the FSHβ coding sequence, what was the construct's unpaired splice-donor site is functionally paired with an endogenous splice-acceptor site of an endogenous exon of FSHβ. Processing of the transcript produced from the homologously recombined FSHβ gene results in splicing of the exogenous exon to the splice-acceptor site of an endogenous exon.

The construct of the invention can also include a splice-acceptor site. This site, in conjunction with a splice-donor site, directs the splicing of one exon to another exon. Splice-acceptor sites have a characteristic sequence represented as $(Y)_{10}NYAG$ (SEQ ID NO:7), where Y denotes any pyrimidine and N denotes any nucleotide (Jackson, Nucleic Acids Research 19:3715–3798, 1991).

Introns

The DNA construct may optionally contain an intron. An intron is a sequence of one or more nucleotides lying between a splice-donor site and a splice-acceptor site, and is removed, by splicing, from a precursor RNA molecule in the formation of a mature mRNA molecule.

The CAP Site

The DNA construct can optionally contain a CAP site. A CAP site is a specific transcription start site which is associated with and utilized by the regulatory region. This CAP site is located at a position relative to the regulatory sequence in the construct such that following homologous recombination, the regulatory sequence directs synthesis of a transcript that begins at the CAP site. Alternatively, no CAP site is included in the construct, and the transcriptional apparatus will locate by default an appropriate site in the targeted gene to be utilized as a CAP site.

Additional DNA elements

The construct may additionally contain sequences which affect the structure or stability of the RNA or protein produced by homologous recombination. optionally, the DNA construct can include a bacterial origin of repliction and bacterial antibiotic resistance markers or other selectable markers, which allow for large-scale plasmid propagation in bacteria or any other suitable cloning/host system.

All of the above-described elements of the DNA construct are operatively linked or functionally placed with respect to each other. That is, upon homologous recombination between the construct and the targeted genomic DNA, the regulatory sequence can direct the production of a primary RNA transcript which initiates at a CAP site (optionally included in the construct) and includes (i) sequence corresponding to the exon and splice-donor site of the construct, if they are present, and (ii) sequence lying between that splice-donor site and the endogenous gene's transcription stop site. The latter sequence may include the FSHβ gene's endogenous regulatory region as well as sequences neighboring that region that are normally not transcribed. In an operatively linked configuration, the splice-donor site of the targeting construct directs a splicing event to a splice-acceptor site flanking one of the exons of the endogenous FSHβ gene, such that a desired protein can be produced from the fully spliced mature transcript. The splice-acceptor site can be endogenous, such that the splicing event is directed to an endogenous exon. In another embodiment where the splice-acceptor site is included in the targeting construct, the splicing event removes the exogenous intron introduced by the targeting construct.

The order of elements in the DNA construct can vary. Where the construct is a circular plasmid or viral vector, the relative order of elements in the resulting structure can be, for example: a targeting sequence, plasmid DNA (comprised of sequences used for the selection and/or replication of the targeting plasmid in a microbial or other suitable host), selectable marker(s), a regulatory sequence, an exon, and an unpaired splice-donor site.

Where the construct is linear, the order can be, for example: a first targeting sequence, a selectable marker gene, a regulatory sequence, an exon, a splice-donor site, and a second targeting sequence; or, in the alternative, a first targeting sequence, a regulatory sequence, an exon, a splice-donor site, a selectable marker gene, and a second targeting sequence. The order of the elements can also be: a first targeting sequence, a selectable marker, a regulatory sequence, an exon, a splice-donor site, an intron, a splice-acceptor site, optionally an internal ribosomal entry site, and second targeting sequence.

Alternatively, the order can be: a first targeting sequence, a first selectable marker gene, a regulatory sequence, an exon, a splice-donor site, a second targeting sequence, and a second selectable marker gene; or, a first targeting sequence, a regulatory sequence, an exon, a splice-donor site, a first selectable marker gene, a second targeting sequence, and a second selectable marker gene. Recombination between the targeting sequences flanking the first selectable marker with homologous sequences in the host genome results in the targeted integration of the first selectable marker, while the second selectable marker is not integrated. Desired transfected or infected cells are those that are stably transfected or infected with the first, but not second, selectable marker. Such cells can be selected for by growth in a medium containing an agent which selects for expression of the first marker and another agent which selects against the second marker. Transfected or infected cells that have improperly integrated the targeting construct by a mechanism other than homologous recombination would be expected to express the second marker gene and will thereby be killed in the medium.

A positively selectable marker is sometimes included in the construct to allow for the selection of cells containing amplified copies of that marker. In this embodiment, the order of construct components can be, for example: a first targeting sequence, an amplifiable positively selectable marker, a second selectable marker (optional), a regulatory sequence, an exon, a splice-donor site, and a second targeting DNA sequence.

The various elements of the construct can be obtained from natural sources (e.g., genomic DNA), or can be produced using genetic engineering techniques or synthetic processes. The regulatory region, CAP site, exon, splice-donor site, and optional intron and splice acceptor site of the construct can be isolated as a complete unit from, e.g., the human elongation factor-1α (Genbank sequence HUMEF1A) gene or the cytomegalovirus (Genbank sequence HEHCMVP1) immediate early region. These components can also be isolated from separate genes.

Transfection or Infection and Homologous Recombination

The DNA construct of the invention can be introduced into the cell, such as a primary, secondary, or immortalized cell, as a single DNA construct, or as separate DNA sequences which become incorporated into the chromosomal or nuclear DNA of a transfected or infected cell. The DNA can be introduced as a linear, double-stranded (with or without single-stranded regions at one or both ends), single-stranded, or circular molecule. The DNA construct or its RNA equivalent can also be introduced as a viral nucleic acid.

When the construct is introduced into host cells in two separate DNA fragments, the two fragments share DNA sequence homology (overlap) at the 3' end of one fragment and the 5' end of the other, while one carries a first targeting sequence and the other carries a second targeting sequence. Upon introduction into a cell, the two fragments can undergo homologous recombination to form a single molecule with the first and second targeting sequences flanking the region of overlap between the two original fragments. The product molecule is then in a form suitable for homologous recombination with the cellular target sites. More than two fragments can be used, with each of them designed such that they will undergo homologous recombination with each other to ultimately form a product suitable for homologous recombination with the cellular target sites as described above.

The DNA construct of the invention, if not containing a selectable marker itself, can be co-transfected or co-infected with another construct that contains such a marker. A targeting plasmid may be cleaved with a restriction enzyme at one or more sites to create a linear or gapped molecule prior to transfection or infection. The resulting free DNA ends increase the frequency of the desired homologous recombination event. In addition, the free DNA ends may be treated with an exonuclease to create overhanging 5' or 3' single-stranded DNA ends (e.g., at least 30 nucleotides in length, and preferably 100–1000 nucleotides in length) to increase the frequency of the desired homologous recombination event. In this embodiment, homologous recombination between the targeting sequence and the genomic target will result in two copies of the targeting sequences, flanking the elements contained within the introduced plasmid.

The DNA constructs may be transfected into cells (preferably in vitro) by a variety of physical or chemical methods, including electroporation, microinjection, microprojectile bombardment, calcium phosphate precipitation, liposome delivery, or polybrene- or DEAE dextran-mediated transfection.

The transfected or infected cell is maintained under conditions which permit homologous recombination, as described in the art (see, e.g., Capecchi, Science 24:1288–1292, 1989). By "transfected cell" is meant a cell into which (or into an ancestor of which) a DNA molecule has been introduced by a means other than using a viral vector. By "infected cell" is meant a cell into which (or into an ancestor of which) a DNA or RNA molecule has been introduced using a viral vector. Viruses known to be useful as vectors include adenovirus, adeno-associated virus, Herpes virus, mumps virus, poliovirus, lentivirus, retroviruses, Sindbis virus, and vaccinia viruses such as canary pox virus. When the homologously recombinant cell is maintained under conditions sufficient to permit transcription of the DNA, the regulatory region introduced by the DNA construct will alter transcription of the FSHβ gene.

Homologously recombinant cells (i.e., cells that have undergone the desired homologous recombination) can be identified by phenotypic screening or by analyzing the culture supernatant in enzyme-linked immunosorbent assays (ELISA) for FSHβ. Commercial ELISA kits for detecting FSHβ are available from Accurate Chemical and Scientific (Westbury, N.Y.). Homologously recombinant cells can also be identified by Southern and Northern analyses or by polymerase chain reaction (PCR) screening.

As used herein, the term "primary cells" includes (i) cells present in a suspension of cells isolated from a vertebrate tissue source (prior to their being plated, i.e., attached to a tissue culture substrate such as a dish or flask), (ii) cells present in an explant derived from tissue, (iii) cells plated for the first time, and (iv) cell suspensions derived from these plated cells. Primary cells can also be cells as they naturally occur within a human or an animal.

Secondary cells are cells at all subsequent steps in culturing. That is, the first time that plated primary cells are removed from the culture substrate and replated (passaged), they are referred to herein as secondary cells, as are all cells in subsequent passages. Secondary cell strains consist of secondary cells which have been passaged one or more times. Secondary cells typically exhibit a finite number of mean population doublings in culture and the property of contact-inhibited, anchorage-dependent growth (anchorage-dependence does not apply to cells that are propagated in suspension culture). Primary and secondary cells are not immortalized.

Immortalized cells are cell lines (as opposed to cell strains, with the designation "strain" reserved for primary and secondary cells) that exhibit an apparently unlimited lifespan in culture.

Cells selected for transfection or infection can fall into four types or categories: (i) cells which do not, as obtained, make or contain more than trace amounts of the FSHβ protein, (ii) cells which make or contain the protein but in quantities other than those desired (such as, in quantities less than the level which is physiologically normal for the type of cells as obtained), (iii) cells which make the protein at a level which is physiologically normal for the type of cells as obtained, but are to be augmented or enhanced in their content or production, and (iv) cells in which it is desirable to change the pattern of regulation or induction of a gene encoding the protein.

Primary, secondary and immortalized cells to be transfected or infected by the present method can be obtained from a variety of tissues and include all appropriate cell types which can be maintained in culture. For example, suitable primary and secondary cells include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells, and precursors of these somatic cell types. Where the homologously recombinant cells are to be used in gene therapy, primary cells are preferably obtained from the individual to whom the transfected or infected primary or secondary cells are to be administered. However, primary cells can be obtained from a donor (i.e., an individual other than the recipient) of the same species.

Examples of immortalized human cell lines useful for protein production or gene therapy include, but are not limited to, 2780AD ovarian carcinoma cells (Van der Blick et al., Cancer Res., 48:5927–5932, 1988), A549 (American Type Culture Collection ("ATCC") CCL 185), BeWo (ATCC CCL 98), Bowes Melanoma cells (ATCC CRL 9607), CCRF-CEM (ATCC CCL 119), CCRF-HSB-2 (ATCC CCL 120.1), COLO201 (ATCC CCL 224), COLO205 (ATCC CCL 222), COLO 320DM (ATCC CCL 220), COLO 32OHSR (ATCC CCL 220.1), Daudi cells (ATCC CCL 213), Detroit 562 (ATCC CCL 138), HeLa cells and derivatives of HeLa cells (ATCC CCL 2, 2.1 and 2.2), HCT116 (ATCC CCL 247), HL-60 cells (ATCC CCL 240), HT1080 cells (ATCC CCL 121), IMR-32 (ATCC CCL 127), Jurkat cells (ATCC TIB 152), K-562 leukemia cells (ATCC CCL 243), KB carcinoma cells (ATCC CCL 17), KG-1 (ATCC CCL 246), KG-1a (ATCC CCL 246.1), LS123 (ATCC CCL 255), LS174T (ATCC CCL CL-188), LS180 (ATCC CCL CL-187), MCF-7 breast cancer cells (ATCC BTH 22), MOLT-4 cells (ATCC CRL 1582), Namalwa cells (ATCC CRL 1432), NCI-H498 (ATCC CCL 254), NCI-H508 (ATCC CCL 253), NCI-H548 (ATCC CCL 249), NCI-H716 (ATCC CCL 251), NCI-H747 (ATCC CCL 252), NCI-H1688 (ATCC CCL 257), NCI-H2126 (ATCC CCL 256), Raji cells (ATCC CCL 86), RD (ATCC CCL 136), RPMI 2650 (ATCC CCL 30), RPMI 8226 cells (ATCC CCL 155), SNU-C2A (ATCC CCL 250.1), SNU-C2B (ATCC CCL 250), SW-13 (ATCC CCL 105), SW48 (ATCC CCL 231), SW403 (ATCC CCL 230), SW480 (ATCC CCL 227), SW620 (ATCC CCL 227), SW837 (ATCC CCL 235), SW948 (ATCC CCL 237), SW1116 (ATCC CCL 233), SW1417 (ATCC CCL 238), SW1463 (ATCC CCL 234), T84 (ATCC CCL 248), U-937 cells (ATCC CRL 1593), WiDr (ATCC CCL 218), and WI-38VA13 subline 2R4 cells (ATCC CLL 75.1), as well as heterohybridoma cells produced by fusion of human cells and cells of another species. Secondary human fibroblast strains, such as WI-38 (ATCC CCL 75) and MRC-5 (ATCC CCL 171), may be used. In addition, primary, secondary, or immortalized human cells, as well as primary, secondary, or immortalized cells from other species, can be used for in vitro protein production or gene therapy.

FSHβ-expressing Cells

Homologously recombinant cells of the invention express FSHβ at desired levels and are useful for in vitro production of FSHβ and gene therapy.

Protein Production

Homologously recombinant cells according to this invention can be used for in vitro production of FSHβ. The cells are maintained under conditions, as described in the art, which result in expression of proteins. The FSHβ protein may be purified from cell lysates or cell supernatants. A pharmaceutical composition containing the FSHβ protein can be delivered to a human or an animal by conventional pharmaceutical routes known in the art (e.g., oral, intravenous, intramuscular, intranasal, pulmonary, transmucosal, intradermal, transdermal, rectal, intrathecal, subcutaneous, intraperitoneal, or intralesional). Oral administration may require use of a strategy for protecting the protein from degradation in the gastrointestinal tract: e.g., by encapsulation in polymeric microcapsules.

Gene Therapy

Homologously recombinant cells of the present invention are useful as populations of homologously recombinant cell lines, as populations of homologously recombinant primary or secondary cells, as homologously recombinant clonal cell strains or lines, as homologously recombinant heterogenous cell strains or lines, and as cell mixtures in which at least one representative cell of one of the four preceding categories of homologously recombinant cells is present. Such cells may be used in a delivery system for treating infertility, for enhancing fertility in a human or animal, or for treating any other conditions treatable with FSHβ.

Homologously recombinant primary cells, clonal cell strains or heterogenous cell strains are administered to an individual in whom the abnormal or undesirable condition is to be treated or prevented, in sufficient quantity and by an appropriate route, to express or make available the protein or exogenous DNA at physiologically relevant levels. A physiologically relevant level is one which either approximates the level at which the product is normally produced in the body or results in improvement of the abnormal or undesirable condition. If the cells are syngeneic with respect to a immunocompetent recipient, the cells can be administered or implanted intravenously, intraarterially, subcutaneously, intraperitoneally, intraomentally, subrenal capsularly, intrathecally, intracranially, or intramuscularly.

If the cells are not syngeneic and the recipient is immunocompetent, the homologously recombinant cells to be administered can be enclosed in one or more semipermeable barrier devices. The permeability properties of the device are such that the cells are prevented from leaving the device upon implantation into a subject, but the therapeutic protein is freely permeable and can leave the barrier device and enter the local space surrounding the implant or enter the systemic circulation. See, e.g., U.S. Pat. Nos. 5,641,670, 5,470,731, 5,620,883, 5,487,737, and co-owned U.S. Patent Application entitled "Delivery of Therapeutic Proteins" (inventors: Justin C. Lamsa and Douglas A. Treco), filed Apr. 16, 1999, all herein incorporated by reference. The barrier device can be implanted at any appropriate site: e.g., intraperitoneally, intrathecally, subcutaneously, intramuscularly, within the kidney capsule, or within the omentum.

Barrier devices are particularly useful and allow homologously recombinant immortalized cells, homologously recombinant cells from another species (homologously recombinant xenogeneic cells), or cells from a nonhistocompatibility-matched donor (homologously recombinant allogeneic cells) to be implanted for treatment of a subject. The devices retain cells in a fixed position in vivo, while protecting the cells from the host's immune system. Barrier devices also allow convenient short-term (i.e., transient) therapy by allowing ready removal of the cells when the treatment regimen is to be halted for any reason. Transfected or infected xenogeneic and allogeneic cells may also be used in the absence of barrier devices for short-term gene therapy. In that case, the FSHβ produced by the cells will be delivered in vivo until the cells are rejected by the host's immune system.

A number of synthetic, semisynthetic, or natural filtration membranes can be used for this purpose, including, but not limited to, cellulose, cellulose acetate, nitrocellulose, polysulfone, polyvinylidene difluoride, polyvinyl chloride polymers and polymers of polyvinyl chloride derivatives. Barrier devices can be utilized to allow primary, secondary, or immortalized cells from another species to be used for gene therapy in humans.

Another type of device useful in the gene therapy of the invention is an implantable collagen matrix in which the cells are embedded. Such a device, which can contain beads to which the cells attach, is described in WO 97/15195, herein incorporated by reference.

The number of cells needed for a given dose or implantation depends on several factors, including the expression level of the protein, the size and condition of the host animal, and the limitations associated with the implantation procedure. Usually the number of cells implanted in an adult human or other similarly-sized animal is in the range of $1 \times 10^4$ to $5 \times 10^{10}$, and preferably $1 \times 10^8$ to $1 \times 10^9$. If desired, they may be implanted at multiple sites in the patient, either at one time or over a period of months or years. The dosage may be repeated as needed.

Other Embodiments

It is to be understood that while the invention has been described in conjunction with the detailed description thereof, the foregoing description is intended to illustrate and not to limit the scope of the invention, which is defined by the scope of the appended claims.

Other aspects, advantages, and modifications are within the scope of the following claims.

What is claimed is:

1. A DNA construct that alters expression of an endogenous FSHβ gene in a mammalian cell upon integration into the genome of the cell via homologous recombination, the construct comprising a targeting sequence containing at least 20 contiguous nucleotides from SEQ ID NO:4 and at least 20 contiguous nucleotides from SEQ ID NO:5, and a transcriptional regulatory sequence.

2. The DNA construct of claim 1, wherein the construct further comprises an exon and a splice-donor site.

3. The DNA construct of claim 2, wherein the construct further comprises, downstream from the splice-donor site, an intron and a splice-acceptor site.

4. A homologously recombinant cell stably transfected with the DNA construct of claim 3, the DNA construct having undergone homologous recombination with genomic DNA upstream of the ATG initiation codon of an endogenous FSHβ coding sequence.

5. A method of producing FSHβ, comprising
providing the cell of claim 4, and
culturing the cell in vitro under conditions which permit the cell to express and secrete FSHβ.

6. A homologously recombinant cell stably transfected with the DNA construct of claim 2, the DNA construct having undergone homologous recombination with genomic DNA upstream of the ATG initiation codon of an endogenous FSHβ coding sequence.

7. A method of producing FSHβ comprising
providing the cell of claim 6, and
culturing the cell in vitro under conditions which permit the cell to express and secrete FSHβ.

8. The DNA construct of claim 1, wherein the construct further comprises a selectable marker gene.

9. A homologously recombinant cell stably transfected with the DNA construct of claim 8, the DNA construct having undergone homologous recombination with genomic DNA upstream of the ATG initiation codon of an endogenous FSHβ coding sequence.

10. A method of producing FSHβ, comprising
providing the cell of claim 9, and
culturing the cell in vitro under conditions which permit the cell to express and secrete FSHβ.

11. The DNA construct of claim 1, wherein the targeting sequence contains at least 50 contiguous nucleotides from SEQ ID NO:4 or 5.

12. A homologously recombinant cell stably transfected with the DNA construct of claim 1, the DNA construct having undergone homologous recombination with genomic DNA upstream of the ATG initiation codon of an endogenous FSHβ coding sequence.

13. A method of producing FSHβ, comprising
providing the cell of claim 12, and
culturing the cell in vitro under conditions which permit the cell to express and secrete FSHβ.

14. A method of altering expression of an endogenous FSHβ gene in a mammalian cell in vitro, the method comprising
introducing the DNA construct of claim 1 into the cell;
maintaining the cell under conditions which permit homologous recombination to occur between the construct and a genornic target site homologous to the targeting sequence, to produce a homologously recombinant cell; and
maintaining the homologously recombinant cell under conditions which permit expression of the FSHβ coding sequence under the control of the transcriptional regulatory sequence.

15. An isolated nucleic acid comprising at least 100 contiguous nucleotides of SEQ ID NO:4 or its complement.

16. The isolated nucleic acid of claim 15, wherein the isolated nucleic acid comprises at least 200 contiguous nucleotides of SEQ ID NO:4 or its complement.

17. The isolated nucleic acid of claim 15, wherein the isolated nucleic acid comprises at least 500 contiguous nucleotides of SEQ ID NO:4 or its complement.

18. The isolated nucleic acid of claim 15, wherein the isolated nucleic acid comprises at least 1000 contiguous nucleotides of SEQ ID NO:4 or its complement.

19. The isolated nucleic acid of claim 15, wherein the isolated nucleic acid comprises SEQ ID NO:4 or its complement.

20. An isolated nucleic acid comprising at least 50 contiguous nucleotides of SEQ ID NO:5 or its complement.

21. The isolated nucleic acid of claim 20, wherein the isolated nucleic acid comprises at least 100 contiguous nucleotides of SEQ ID NO:5 or its complement.

22. The isolated nucleic acid of claim 20, wherein the isolated nucleic acid comprises at least 200 contiguous nucleotides of SEQ ID NO:5 or its complement.

23. The isolated nucleic acid of claim 20, wherein the isolated nucleic acid comprises SEQ ID NO:5 or its complement.

24. A DNA construct that alters expression of an endogenous FSHβ gene in a mammalian cell upon integration into the genome of the cell via homologous recombination, the construct comprising a targeting sequence containing at least 20 contiguous nucleotides from SEQ ID NO:5 and a transcriptional regulatory sequence.

25. The DNA construct of claim 24, wherein the construct further comprises a exon and a splice-donor site.

26. The DNA construct of claim 25, wherein the construct further comprises, downstream from the splice-donor site, an intron and a splice-acceptor site.

27. A homologously recombinant cell stably tsfected with the DNA construct of claim 26, the DNA construct having undergone homologous recombination with genomic DNA upstream of the ATG initiation codon of an endogenous FSHβ coding sequence.

28. A method of producing FSHβ, comprising providing the cell of claim 27, and culturing the cell in vitro under conditions which permit the cell to express and secrete FSHβ.

29. A homologously recombinant cell stably transfected with the DNA construct of claim 25, the DNA construct having undergone homologous recombination with genomic DNA upstream of the ATG initiation codon of an endogenous FSHβ coding sequence.

30. A method of producing FSHβ, comprising providing the cell of claim 29, and culturing the cell in vitro under conditions which permit the cell to express and secrete FSHβ.

31. The DNA construct of claim 24, wherein the construct further comprises a selectable marker gene.

32. A homologously recombinant cell stably transfected with the DNA construct of claim 31, the DNA construct having undergone homologous recombination with genomic DNA upstream of the ATG initiation codon of an endogenous FSHβ coding sequence.

33. A method of producing FSHβ, comprising providing the cell of claim 32, and culturing the cell in vitro under conditions which permit the cell to express and secrete FSHβ.

34. The DNA construct of claim 24, wherein the targeting sequence contains at least 50 contiguous nucleotides from SEQ ID NO:5.

35. A homologously recombinant cell stably transfected with the DNA construct of claim 24, the DNA construct having undergone homologous recombination with genomic DNA upstream of the ATG initiation codon of an endogenous FSHβ coding sequence.

36. A method of producing FSHβ, comprising providing the cell of claim 35, and culturing the cell in vitro under conditions which permit the cell to express and secrete FSHβ.

37. A method of altering expression of an endogenous FSHβ gene in a mammalian cell in vitro, the method comprising, introducing the DNA construct of claim 24, into the cell;

maintaining the cell under conditions which permit homologous recombination to occur between the construct and a genomic target site homologous to the targeting sequence, to produce a homologously recombinant cell; and maintaining the homologously recombinant cell under conditions which permit expression of the FSHβ coding sequence under the control of the transcriptional regulatory sequence.

\* \* \* \* \*

UNITED STATES PATENT AND TRADEMARK OFFICE
CERTIFICATE OF CORRECTION

PATENT NO. : 6,200,778 B1
DATED : March 13, 2001
INVENTOR(S) : Douglas A. Treco, Michael W. Heartlein and Richard F. Selden It is certified that error appears in the above-identified patent and that said Letters Patent is hereby corrected as shown below:

Title page,
Under the heading "OTHER PUBLICATIONS", in the "Esch et al." reference. Replace "6681-6621" with -- 6618-6621 --.

Column 4,
Line 20, "PSHβ-coding" should be -- FSHβ-coding --

Column 9,
Line 29, "Seauences" should be -- Sequences --
Line 65, "Seauence" should be -- Sequence --

Column 12,
Line 6, "optionally" should be -- Optionally --

Column 34,
Line 37, "genornic" should be -- genomic --

Column 35,
Line 12, "tsfected" should be -- transfected --

Signed and Sealed this

Seventh Day of May, 2002

*Attest:*

*Attesting Officer*

JAMES E. ROGAN
*Director of the United States Patent and Trademark Office*